(12) United States Patent
Yang et al.

(10) Patent No.: US 11,788,105 B2
(45) Date of Patent: Oct. 17, 2023

(54) POLYPEPTIDES WITH LIPASE ACTIVITY AND USES THEREOF

(71) Applicant: Wilmar International Limited, Singapore (SG)

(72) Inventors: Ren Liang Yang, Singapore (SG); Hong Fang Zhang, Singapore (SG); Weijian Ye, Singapore (SG); Mong Jie Andre Ng, Singapore (SG); Kien Truc Giang Nguyen, Singapore (SG)

(73) Assignee: Wilmar International Limited, Singapore (SG)

( * ) Notice: Subject to any disclaimer, the term of this patent is extended or adjusted under 35 U.S.C. 154(b) by 51 days.

(21) Appl. No.: 17/137,887

(22) Filed: Dec. 30, 2020

(65) Prior Publication Data

US 2021/0198704 A1    Jul. 1, 2021

(30) Foreign Application Priority Data

Dec. 31, 2019   (SG) .......................... 10201914033Y

(51) Int. Cl.
*C12P 7/6418* (2022.01)
*C12P 21/02* (2006.01)

(52) U.S. Cl.
CPC ............. *C12P 7/6418* (2013.01); *C12P 21/02* (2013.01)

(58) Field of Classification Search
CPC ............................. C12P 7/6418; C12P 21/02
See application file for complete search history.

(56) References Cited

U.S. PATENT DOCUMENTS

| | | |
|---|---|---|
| 4,469,863 A | 9/1984 | Ts'o et al. |
| 5,023,243 A | 6/1991 | Tullis |
| 5,130,302 A | 7/1992 | Spielvogel et al. |
| 5,177,198 A | 1/1993 | Spielvogel et al. |
| 5,223,618 A | 6/1993 | Cook et al. |
| 5,256,775 A | 10/1993 | Froehler |
| 5,264,562 A | 11/1993 | Matteucci |
| 5,264,564 A | 11/1993 | Matteucci |
| 5,366,878 A | 11/1994 | Pederson et al. |
| 5,378,825 A | 1/1995 | Cook et al. |
| 5,386,023 A | 1/1995 | Sanghvi et al. |
| 5,476,925 A | 12/1995 | Letsinger et al. |
| 5,489,677 A | 2/1996 | Sanghvi et al. |
| 5,508,270 A | 4/1996 | Baxter et al. |
| 5,602,240 A | 2/1997 | De Mesmaeker et al. |
| 5,610,289 A | 3/1997 | Cook et al. |
| 5,625,050 A | 4/1997 | Beaton et al. |
| 2008/0090280 A1* | 4/2008 | Schnorr ......... C12Y 302/01032 435/325 |

FOREIGN PATENT DOCUMENTS

| | | |
|---|---|---|
| WO | 9402499 | 2/1994 |
| WO | 9417093 | 8/1994 |

OTHER PUBLICATIONS

Abramić, M., Leščić, I., Korica, T., Vitale, L., Saenger, W., & Pigac, J. (1999). Purification and properties of extracellular lipase from Streptomyces rimosus. Enzyme and Microbial Technology, 25(6), 522-529 (Year: 1999).*
Sun, S., Liu, J., & Li, X. (2018). A novel and rapid method for fatty acid preparation by the lipase-catalyzed hydrolysis of Phoenix tree seeds. 3 Biotech, 8(9), 1-8. (Year: 2018).*
Genscript, Parts per million (ppm), Biology Terms Dictionary, [serial online], accessed from https://www.genscript.com/biology-glossary/10863/Parts-per-million-ppm (Year: 2022).*
Kapoor, M., & Gupta, M. N. (2012). Lipase promiscuity and its biochemical applications. Process Biochemistry, 47(4), 555-569. (Year: 2012).*

* cited by examiner

*Primary Examiner* — Robert J Yamasaki
*Assistant Examiner* — Trevor L Kane
(74) *Attorney, Agent, or Firm* — Jones Robb, PLLC

(57) ABSTRACT

Described are methods of using a lipase for hydrolysis and esterification. In a first method of producing a medium chain fatty acid by hydrolysis, the method comprises providing a polypeptide with at least 90% degree of identity to SEQ ID No. 3, and contacting the polypeptide with a medium chain fatty acid ester and water to produce the medium chain fatty acid. In a second method of forming an ester, the method comprises providing a polypeptide with at least 90% degree of identity to SEQ ID No. 3; and contacting the polypeptide with a long chain fatty acid, an alcohol, and water to form the ester of the long chain fatty acid and the alcohol.

7 Claims, 7 Drawing Sheets

Specification includes a Sequence Listing.

POLYPEPTIDES WITH LIPASE ACTIVITY AND USES THEREOF

TECHNICAL FIELD

The present invention provides polypeptides with lipase activity, polynucleotides encoding the polypeptides, methods of producing the polypeptides, and uses of the polypeptides.

BACKGROUND

Lipases are widely distributed in plants, animals and microorganisms. Microbial lipases have been widely used for their activity under a wide range of pH and temperature as well as the substrate specificity of lipases from some microbes.

Lipases have multiple catalytic capabilities, for the hydrolysis of triacylglyceride into glycerol and free fatty acids, the hydrolysis and/or transesterification of esters, and the synthesis of esters from glycerol and free fatty acids. Lipases have been widely used in industries of food processing, oil processing, biodiesel production, detergent preparation, the synthesis of ester bond compounds and chiral drug (Abhishek Kumar Singh, Mausumi Mukhopadhyay, Overview of Fungal Lipase: A Review, 2012, 166(2):486-520), etc. Among the applications of lipases in the chemical industry, the hydrolysis of methyl octanoate (C8 methyl ester) or methyl decanoate (C10 methyl ester), the hydrolysis of castor oil or hydrogenated castor oil, and the production of biodiesel have gathered lots of attention and efforts. However, different lipases may have different specifities and/or level of activities for different substrates and/or reactions, as such it is often not possible to predict the specificity or selectivity of a lipase.

The most widely used commercial lipases for the hydrolysis of methyl octanoate or methyl decanoate are lipases derived from *Rhizomucor miehei* and *Candida Antarctica*. However, industrial applications of these enzymatic process are limited by high prices of these lipases. Therefore, new lipases with high enzyme activity and potentially cheaper price are needed for the application of lipases in chemical industry, such as the industrial applications of lipases in the hydrolysis of fatty acid methyl esters, such as methyl octanoate or methyl decanoate.

The most widely used commercial lipases for the production of biodiesel are lipases from Novozyme® 435 (from *Candida antartica*) and Eversa® Transform 2.0 (from *Thermomyces lanuginosus*, hereinafter Eversa®). Similarly, to promote the industrial application of lipase in the production of biodiesel, new lipases with high specific enzyme activity and potentially cheaper price are needed.

Accordingly, the objectives are to screen and develop novel polypeptides with lipase activity. Some of the lipases have high efficiency in catalyzing the hydrolysis of methyl octanoate or methyl decanoate or the like or in catalyzing the production of biodiesel to meet the needs of industrial production.

SUMMARY

Described herein are isolated polypeptides with lipase activity, isolated polynucleotides encoding the polypeptides, methods for producing the polypeptides, and uses or applications of the polypeptides.

Some of the polypeptides have a preference for medium to short chain fatty acid esters, and may be used for the hydrolysis of short to medium chain fatty acid esters, such as C4-C12 fatty acid esters. More specifically, some of the polypeptides m used for catalyzing the hydrolysis of methyl octanoate or methyl decanoate.

Some of the polypeptides described are excellent in catalyzing transesterification or esterification reactions for the production of biodiesel.

In a first aspect, there is provided isolated polypeptides with lipase activity, selected from the group consisting of:
1) a polypeptide having amino acid sequence of SEQ ID NO:1 or SEQ ID NO:3,
2) a polypeptide having amino acid sequence of SEQ ID NO:1 or SEQ ID NO:3 and sequence for promoting the expression and purification of said SEQ ID NO:1 or SEQ ID NO:3, and
3) a polypeptide which is a fragment or a derivative of any of the polypeptides of 1) or 2), wherein the fragment or derivative has lipase activity.

The polypeptides of the present invention also include polypeptides having at least 90%, preferentially at least 95%, more preferentially at least 98%, even more preferentially at least 99% sequence identity to the polypeptide of SEQ ID NO:1 or SEQ ID NO:3.

The polypeptides of SEQ ID NO:1 and SEQ ID NO:3 may be derived from *Thielavia terrestris* and *Lasiodiplodia theobromae* respectively.

In a second aspect, there is provided an isolated polynucleotide selected from the group consisting of:
a) a polynucleotide encoding the polypeptide of the present invention;
b) a polynucleotide that are complementary to the polynucleotide of a); and
c) a polynucleotide fragment of a) or b) containing 10 to 40 base pairs.

In one or more embodiments, the polynucleotide comprises nucleic acid sequence of SEQ ID NO:2 or SEQ ID NO:4.

In one or more embodiments, the polynucleotide consists of nucleic acid sequence of SEQ ID NO:2 or SEQ ID NO:4.

In one or more embodiments, the polynucleotide may be a genomic DNA, cDNA, synthetic DNA, or a combination thereof.

In a third aspect, there is provided a nucleic acid construct, which comprises the polynucleotide of the present invention.

In one or more embodiments, said nucleic acid construct comprises one or more polynucleotides encoding the polypeptides of the present invention, or one or more polynucleotides complimentary to the polynucleotides encoding the polypeptides of the present invention.

In one or more embodiments, said nucleic acid construct comprises nucleic acid sequence chosen from SEQ ID NO:2 or SEQ ID NO:4, or complimentary sequences thereof.

In one or more embodiments, said nucleic acid construct is a vector, such as a cloning vector or an expression vector.

In one or more embodiments, said nucleic acid construct comprises AOX1 promoter, signal peptide α-Factor, expression frame His4, and multiple cloning sites.

In one or more embodiments, said nucleic acid construct has pPIC9K plasmid as its backbone.

In a fourth aspect, there is provided a recombinant cell or a host cell, which comprises the nucleic acid construct of the third aspect.

In one or more embodiments, said recombinant cell is a plant cell.

In one or more embodiments, said recombinant cell is a microorganism cell.

In one or more embodiments, said recombinant cell is a *Pichia pastoris* cell, or an *Escherichia coli* cell.

In a fifth aspect, there is provided a composition comprising the polypeptide with lipase activity according to the first aspect, or the host cell according to the fourth aspect, and optionally excipients.

In one or more embodiments, said excipients are adsorbent materials chosen from activated carbon, alumina, diatomaceous earth, porous ceramics, porous glass, and so on.

In a sixth aspect, there is provided a method of producing a fatty acid, in particular a medium chain fatty acid. The method includes providing a polypeptide having at least 90% degree of identity to SEQ ID No. 3; contacting the polypeptide with a fatty acid ester (preferably a medium chain fatty acid ester) and water to produce the fatty acid. Preferably, the polypeptide has a 95% degree of identity to SEQ ID No. 3, more preferably 98%, 99% or 100%.

In one or more embodiments, said fatty acid methyl ester is a monoester. For example, wherein the medium chain fatty acid ester is at least one selected from a caprylate ester (octanoate ester), a caprate ester (decanoate ester), and a laurate ester (dodecanoate ester). Preferably, the ester is a methyl ester or ethyl ester. For example, the ester may be methyl octanoate or methyl decanoate or a mixture thereof.

The contacting step may be performed under one of the following conditions:

A) a temperature of 20° C. and 70° C., preferably 30° C. and 40° C.;
B) a pH of 3 and 9, or 5.5 and 9.0, or 6.0 and 9.0;
C) a pressure of 100 mbar and lower.

In an embodiment, the polypeptide is present in a concentration (or dosage) of 30 ppm or greater. The polypeptide may be added in a single batch or multiple batches.

In an example, the product formed may have an acid value (AV) of at least 320. In another example, the acid value is at least 330. In another example, the acid value is at least 340.

In a seventh aspect, there is provided a reaction mixture for hydrolysis, characterized in that the reaction mixture comprises one or more fatty acid esters, water, and the polypeptide according to the first aspect, the host cell according to the fourth aspect, or the composition according to the fifth aspect.

In one or more embodiments, the polypeptide may be present in a concentration of 30 ppm or greater, or preferably 40 ppm or higher. The polypeptide may be added as a single or multiple dose.

One lipase unit is defined as the quantity of enzyme that will liberate 1 μmol of fatty acid per minute under the conditions of the test (pH 8.0 and 37° C.). The substrates used for unit activity calculation are tributyrin, vinyl laurate or olive oil.

In an eighth aspect, there is provided a method of forming an ester, the method includes providing a polypeptide with at least 90% degree of identity to SEQ ID No. 3; and contacting the polypeptide with a long chain fatty acid, an alcohol, and water to form the ester of the long chain fatty acid and the alcohol. Preferably, the polypeptide has a 95% degree of identity to SEQ ID No. 3, more preferably 98%, 99% or 100%.

The long chain fatty acid may be provided as oils (in particular acid oil), tallows or palm free fatty acid distillate (PFAD). The alcohol may be a C1-C4 alcohol, for example methanol or ethanol. A C1-C4 alcohol refers to a compound having one to four carbon atoms (i.e. the C1 term refers to one carbon atom and so forth) and at least one hydroxyl group. The polypeptide may be according to the first aspect, the host cell according to the fourth aspect, or the composition according to the fifth aspect. The ester may be used for the production of biodiesel, the process comprises one or more steps for the substrate to be in contact with the polypeptide according to the first aspect, the host cell according to the fourth aspect, or the composition according to the fifth aspect. Advantageously, the use of PFAD or acid oil which are by-products normally discarded provides for greater sustainability and efficiency of the process.

In an embodiment, a long chain fatty acid ester may be used in the contacting step. The long chain fatty acid ester may aid the solubility of the fatty acid.

In an embodiment, a base may be used in the contacting step. The base may advantageously allow the fatty acid to ionise and to increase the activity of the lipase. The base may be an inorganic base, an organic base, or a polymer supported base. Examples of inorganic bases that may be used include hydroxides, like sodium hydroxide or potassium hydroxide.

In an embodiment, the water is present in 3 to 12 weight percent relative to the weight of the long chain fatty acid and optionally the long chain fatty ester if present.

In an embodiment, the polypeptide is present in a concentration of at least 20 ppm. The polypeptide may be added as a single or multiple dose.

In a ninth aspect, there is provided an application of the isolated polypeptide according to the first aspect, the recombinant cells according to the forth aspect, or the compositions according to the fifth aspect, in oil refining, oleochemical industry, chemical industry, feeds production, food preparation, medicine preparation, biodiesel preparation, or in the hydrolysis of fatty acid methyl esters.

Further described are processes for the hydrolysis of lipids, the transesterification of esters, or the synthesis of esters, which involve the use of the isolated polypeptides according to the first aspect, the recombinant cells according to the forth aspect, or the compositions according to the fifth aspect.

Further described is the application of the polypeptide according to the first aspect in the hydrolysis of a lipid, such as methyl fatty acid ester (methyl octanoate or methyl decanoate), castor oil, and hydrogenated castor oil, and in the production of biodiesel.

FIGURES

DETAILED DESCRIPTION

Figure 1A:
FIG. 1A shows the comparison of positive transformant GS115(P9K-TTL) on the left with the control GS115 without being transformed vectors on the right. The clearing and calcium deposition, i.e. halo, around the positive transformant GS115(P9K-TTL) shows the recombinant strain has lipase activity.

Unless defined otherwise or the context clearly dictates otherwise, all technical and Scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention, as are ranges based thereon.

The word "substantially" does not exclude "completely" e.g. a composition which is "substantially free" from Y may be completely free from Y. Where necessary, the word "substantially" may be omitted from the definition of the invention.

Although each of these terms has a distinct meaning, the terms "comprising", "consisting of" and "consisting essentially of" may be interchanged for one another throughout the instant application. The term "having" has the same meaning as "comprising" and may be replaced with either the term "consisting of" or "consisting essentially of".

The term "corresponding mRNA" refers to mRNA which was or can be a template for cDNA synthesis for producing a cDNA of the present invention.

The term "corresponding genomic DNA" refers to genomic DNA which encodes an mRNA of interest, e.g. corresponding to a cDNA of the invention, which genomic DNA includes the sequence of one of the strands of the mRNA, in which thymidine residues in the sequence of the genomic DNA (or cDNA) are replaced by uracil residues in the mRNA.

The term "isolated" with respect to a molecule requires that the molecule be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment. For example, a naturally-occurring polynucleotide present in a living animal is not isolated, but the same polynucleotide, separated from some or all of the coexisting materials in the natural system, is isolated. Specifically excluded from the definition of "isolated" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified polynucleotide makes up less than 5% (may also be specified as 10%, 25%, 50%, or 75%) of the number of nucleic acid inserts in the vector molecules. Further specifically excluded are whole cell genomic DNA or whole cell RNA preparations (including said whole cell preparations which are mechanically sheared or enzymatically digested). Further specifically excluded are the above whole cell preparations as either an in vitro preparation or as a heterogeneous mixture separated by electrophoresis (including blot transfers of the same) wherein the polynucleotide of the invention has not further been separated from the heterologous polynucleotides in the electrophoresis medium (e.g., further separating by excising a single band from a heterogeneous band population in an agarose gel or nylon blot).

The term "purified" does not require absolute purity; rather, it is intended as a relative definition. Purification of starting material or natural material to at least one order of magnitude, preferably two or three orders, and more preferably four or five orders of magnitude is expressly contemplated. The term "purified" is further used herein to describe a polypeptide or polynucleotide of the invention which has been separated from other compounds including, but not limited to, polypeptides or polynucleotides, carbohydrates, lipids, etc. The term "purified" may be used to specify the separation of monomeric polypeptides of the invention from oligomeric forms such as homo- or heterodimers, trimers, etc. The term "purified" may also be used to specify the separation of covalently closed (i.e. circular) polynucleotides from linear polynucleotides. A substantially pure polypeptide or polynucleotide typically comprises about 50%, preferably 60 to 90% weight/weight of a polypeptide or polynucleotide sample, respectively, more usually about 95%, and preferably is over about 99% pure but, may be specified as any integer of percent between 50 and 100. Polypeptide and polynucleotide purity, or homogeneity, is indicated by a number of means well known in the art, such as agarose or polyacrylamide gel electrophoresis of a sample, followed by visualizing a single band upon staining the gel. For certain purposes higher resolution can be provided by using HPLC or other means well known in the art. As an alternative embodiment, purification of the polypeptides and polynucleotides of the present invention may be expressed as "at least" a percent purity relative to heterologous polypeptides and polynucleotides (DNA, RNA or both). As a preferred embodiment, the polypeptides and polynucleotides of the present invention are at least; 10%, 20%, 30%, 40%, 50%, 60%, 70%, 80%, 90%, 95%, 96%, 96%, 98%, 99%, or 100% pure relative to heterologous polypeptides and polynucleotides, respectively. As a further preferred embodiment the polypeptides and polynucleotides have a purity ranging from any number, to the thousandth position, between 90% and 100% (e.g., a polypeptide or polynucleotide at least 99.995% pure) relative to either heterologous polypeptides or polynucleotides, respectively, or as a weight/weight ratio relative to all compounds and molecules other than those existing in the carrier. Each number representing a percent purity, to the thousandth position, may be claimed as individual species of purity.

As used interchangeably herein, the terms "nucleic acid molecule(s)", "oligonucleotide(s)", and "polynucleotide(s)" include RNA or DNA (either single or double stranded, coding, complementary or antisense), or RNA/DNA hybrid sequences of more than one nucleotide in either single chain or duplex form (although each of the above species may be particularly specified). The term "nucleotide" is used herein as an adjective to describe molecules comprising RNA, DNA, or RNA/DNA hybrid sequences of any length in single-stranded or duplex form. More precisely, the expression "nucleotide sequence" encompasses the nucleic material itself and is thus not restricted to the sequence information (i.e. the succession of letters chosen among the four base letters) that biochemically characterizes a specific DNA or RNA molecule. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one modification such as (a) an alternative linking group, (b) an analogous form of purine, (c) an analogous form of pyrimidine, or (d) an analogous sugar. For examples of analogous linking groups, purine, pyrimidines, and sugars, see, for example, PCT publication No. WO 95/04064, which disclosure is hereby incorporated by reference in its entirety. Preferred modifications of the present invention include, but are not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methyl cytosine, 5-methyl cytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v) ybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, and 2,6-diaminopurine. The polynucleotide sequences of the invention may be prepared by any known method, including synthetic, recombinant, ex vivo generation, or a combination thereof, as well as utilizing any purification methods known in the art. Methylenemethylimino linked oligonucleosides as well as mixed backbone compounds having, may be prepared as described in U.S. Pat. Nos. 5,378,825; 5,386,023; 5,489,677; 5,602,240; and 5,610,289, which disclosures are hereby incorporated by reference in their entireties. Formacetal and thioformacetal linked oligonucleosides may be prepared as described in U.S. Pat. Nos. 5,264,562 and 5,264,564, which disclosures are hereby incorporated by reference in their entireties. Ethylene oxide linked oligonucleosides may be prepared as described in U.S. Pat. No. 5,223,618, which disclosure is hereby incorporated by reference in its entirety. Phosphinate oligonucleotides may be prepared as described in U.S. Pat. No. 5,508,270, which disclosure is hereby incorporated by reference in its entirety. Alkyl phosphonate oligonucleotides may be prepared as described in U.S. Pat. No. 4,469,863, which disclosure is hereby incorporated by reference in its entirety. 3'-Deoxy-3'-methylene phosphonate oligonucleotides may be prepared as described in U.S. Pat. No. 5,610,289 or 5,625,050 which disclosures are hereby incorporated by reference in their entireties. Phosphoramidite oligonucleotides may be prepared as described in U.S. Pat. No. 5,256,775 or U.S. Pat. No. 5,366,878 which disclosures are hereby incorporated by reference in their entireties. Alkylphosphonothioate oligonucleotides may be prepared as described in published PCT applications WO 94/17093 and WO 94/02499 which disclosures are hereby incorporated by reference in their entireties. 3'-Deoxy-3'-amino phosphoramidate oligonucleotides may be prepared as described in U.S. Pat. No. 5,476,925, which disclosure is hereby incorporated by reference in its entirety. Phosphotriester oligonucleotides may be prepared as described in U.S. Pat. No. 5,023,243, which disclosure is hereby incorporated by reference in its entirety. Borano phosphate oligonucleotides may be prepared as described in U.S. Pat. Nos. 5,130,302 and 5,177,198 which disclosures are hereby incorporated by reference in their entireties.

The terms "polypeptide" and "protein", used interchangeably herein, refer to a polymer of amino acids without regard to the length of the polymer; thus, peptides, oligopeptides, and proteins are included within the definition of polypeptide. This term also does not specify or exclude chemical or post-expression modifications of the polypeptides of the invention, although chemical or post-expression modifications of these polypeptides may be included or excluded as specific embodiments. Therefore, for example, modifications to polypeptides that include the covalent attachment of glycosyl groups, acetyl groups, phosphate groups, lipid groups and the like are expressly encompassed by the term polypeptide. Further, polypeptides with these modifications may be specified as individual species to be included or excluded from the present invention. The natural or other chemical modifications, such as those listed in examples above can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. [See, for instance Creighton, (1993), Posttranslational Covalent Modification of Proteins, W.H. Freeman and Company, New York B. C. Johnson, Ed., Academic Press, New York 1-12; Seifter, et al., (1990) Meth Enzymol 182:626-646; Rattan et al., (1992) Ann NY Acad Sci 663:48-62]. Also included within the definition are polypeptides which contain one or more analogs of an amino acid (including, for example, non-naturally occurring amino acids, amino acids which only occur naturally in an unrelated biological system, modified amino acids from mammalian systems, etc.), polypeptides with substituted linkages, as well as other modifications known in the art, both naturally occurring and non-naturally occurring.

As used herein, the terms "recombinant polynucleotide" and "polynucleotide construct" are used interchangeably to refer to linear or circular, purified or isolated polynucleotides that have been artificially designed and which comprise at least two nucleotide sequences that are not found as contiguous nucleotide sequences in their initial natural environment. In particular, these terms mean that the polynucleotide or cDNA is adjacent to "backbone" nucleic acid to which it is not adjacent in its natural environment. Additionally, to be "enriched" the cDNAs will represent 5% or more of the number of nucleic acid inserts in a population of nucleic acid backbone molecules. Backbone molecules according to the present invention include nucleic acids such as expression vectors, self-replicating nucleic acids, viruses, integrating nucleic acids, and other vectors or nucleic acids used to maintain or manipulate a nucleic acid insert of interest. Preferably, the enriched cDNAs represent 15% or more of the number of nucleic acid inserts in the population of recombinant backbone molecules. More preferably, the enriched cDNAs represent 50% or more of the number of nucleic acid inserts in the population of recombinant backbone molecules. In a highly preferred embodiment, the enriched cDNAs represent 90% or more (including any number between 90 and 100%, to the thousandth position, e.g., 99.5%) of the number of nucleic acid inserts in the population of recombinant backbone molecules.

The terms "degree of identity", "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Identity is evaluated using any of the variety of sequence comparison algorithms and programs known in the art. Such algorithms and programs include, but are by no means limited to, TBLASTN, BLASTP, FASTA, TFASTA, CLUSTAL W, FASTDB [Pearson and Lipman, (1988), Proc. Natl. Acad. Sci. USA 85(8):2444-2448; Altschul et al., (1990), J. Mol. Biol. 215(3):403-410; Thompson et al. (1994), Nucleic Acids Res. 22(2):4673-4680; Higgins et al., (1996), Meth. Enzymol. 266:383-402; Altschul et al., (1993), Nature Genetics 3:266-272; Brutlag et al. (1990) Comp. App. Biosci. 6:237-24], the disclosures of which are incorporated by reference in their entireties.

Polypeptides Having Lipase Activity

The polypeptides having an amino acid sequence of SEQ ID NO: 1 or SEQ ID NO: 3, has been found to have lipase activity. The polypeptides may be modified by conservative substitutions of one or more amino acids with similar amino acids or amino acids of similar properties. The conservative substitutions usually do not change the property of the protein or the polypeptide. "Similar amino acids or amino acids of similar properties" means families of amino acid residues with similar side chains. Amino acid residues with similar side chains for example are amino acids with basic side chains (such as lysine, arginine, histidine), amino acids with acidic side chains (such as aspartic acid, glutamic acid), amino acids with uncharged polar side chains (such as glycine, asparagine, glutamine, serine, threonine, tyrosine, cysteine), amino acids with non-polar side chains (such as alanine, valine, leucine, isoleucine valine, phenylalanine, methionine, tryptophan), amino acids with (3-branched side chains (such as threonine, valine, isoleucine) and amino acids with aromatic side chains (such as, tyrosine, phenylalanine, tryptophan, histidine). Substituting one or more sites of the polypeptide with amino acid residues from the same family would not substantially influence the activity of the polypeptide or the protein.

Polypeptides may be derived from substituting, deleting or adding one or more amino acids from SEQ ID NO: 1 (TTL) or SEQ ID NO: 3 (LTL3), by while retaining the lipase activity of the original polypeptides. These modifications may be up to 10% of the sequence identity of the original sequence, thus providing a polypeptide with at least 90% degree of identity to SEQ ID No. 1 or SEQ ID No. 3. In an example, "more" means less than 10, preferentially less than 8, and even more preferentially less than 5.

Amino acid residues in the sequence of SEQ ID NO: 1 or SEQ ID NO: 3 which may be substituted or deleted can be determined by using conventional techniques, given the sequence and biological functions thereof. For example, by aligning sequences from different species but with the same, similar or distinctly different activity, it is possible to determine which amino acid residues in these sequences could be substituted or deleted. Then the activity of the sequences after modification could be verified by routine methods in the art including methods disclosed in the present invention.

Furthermore, it is often necessary to design suitable cleavage sites in gene cloning operations which introduce one or more other residues at the ends of the expressed protein, such as residues for restriction endonuclease recognition. It is also often necessary to add some amino acids to N-terminus, C-terminus, or other suitable regions of the protein, for constructing a fusion protein, promoting the expression of a recombinant protein, obtaining recombinant protein that is automatically secreted from the host cell, or purifying the recombinant protein. The suitable regions of the protein include but not limited to suitable linker peptides, signal peptides, pro-region peptide, leader peptides, terminal extensions, glutathione S-transferase (GST), maltose E binding protein, protein A, Xa factor or proteolytic enzyme site of thrombin or enterokinase. The amino terminus (N-terminus), or carboxy terminus (C-terminus), of the amino acid sequence may also contain one or more polypeptide fragments as protein tags. Any suitable label may be used. For example, the tags can be FLAG, HA, HAL c-Myc, Poly-His, Poly-Arg, Strep-TagII, AU1, EE, T7, 4A6, ε, B, gE, and Ty1. These tags can be used for protein purification. It should be understood that these tags and labels do not affect the activity of the resulting polypeptide. Accordingly, polypeptides may be obtained by the addition of one or several amino acids at the C-terminus and/or N-terminus of a polypeptide of SEQ ID No. 1 or SEQ ID No. 3, and the polypeptides still maintain the lipase activity.

The polypeptides may have an amino acid sequence which has a degree of identity to the polypeptide of SEQ ID NO: 1 or SEQ ID NO: 3 of at least 90%, preferentially at least 95%, more preferentially at least 98%, even more preferentially at least 99%, which have lipase activity. The sequence identity of two sequences can be calculated using conventional means, for example, BLAST® on NCBI or aligning using default parameters.

In some embodiments, these amino acid sequences are from *Thielavia terrestris* or *Lasiodiplodia theobromae*, preferentially the polypeptides of these amino acid sequences have the same or similar lipase activity as the activity of the polypeptide of SEQ ID NO: 1 or SEQ ID NO: 3.

In some embodiments, the polypeptides are lipases with substrate specificity. In some embodiments, the polypeptides have high hydrolysis efficiency on some substrates. In some embodiments, the polypeptides have an optimum working temperature between 20 and 70° C., preferably between 30° C. and 50° C., more preferably between 35° C. and 45° C. or between 40° C. and 50° C., inclusive of both end points. In some embodiments, the optimum pH for polypeptides is between 5.5 and 9, preferably between 6.5 and 7.5, inclusive of both end points. In some embodiments, the enzyme activity of the polypeptides may be inhibited or strengthened by metal ions. In some embodiments, the polypeptides may have similar levels of hydrolysis activity with some commercial enzymes. In some embodiments, the polypeptides may be used in the hydrolysis of fatty acid methyl esters, such as fatty acid methyl esters with short to medium chain (C4~C12) fatty acid residues, examples include methyl octanoate or methyl decanoate.

In some embodiments, the polypeptides may have high efficiency in the production of biodiesel. In some embodiments, the polypeptides may have an optimum working temperature between 20° C. and 60° C., preferably between 30° C. and 50° C., more preferably between 35° C. and 45° C. or between 40° C. and 50° C., inclusive of both end points. In some embodiments, the optimum pH for polypeptides may be between 5.5 and 9.0, preferably between 6.5 and 7.5, inclusive of both end points. In some embodiments, the enzyme activity of polypeptides may be inhibited or strengthened by metal ions. In some embodiments, the polypeptides may have similar levels of synthesis activity with some commercial enzymes. In some embodiments, the polypeptides may be used in the transesterification or esterification of various substrates to produce fatty acid methyl/ethyl esters as biodiesel, and especially for the preparation of biodiesel from palm free fatty acid distillate (PFAD), mixed vegetable acid oil, used cooking oil, tallow, crude palm oil, vegetable oils and methanol or ethanol.

In some embodiments, the polypeptides may or may not be glycosylated or not glycosylated, depending on the host cell used.

In some embodiments, the polypeptides may be naturally purified, synthesized by chemical means, or produced by recombinant gene technology from prokaryotic or eukaryotic hosts, such as bacteria, yeasts, plants, or mammalian cells.

Polynucleotides Encoding Polypeptides of the Present Invention

Also described are polynucleotides that are coding sequences which encode the polypeptides. SEQ ID NO: 2 and SEQ ID NO: 4, and subsequences thereof are examples of such polynucleotides. "Coding sequences" means nucleotide sequences which are highly homologous to SEQ ID NO: 2 or SEQ ID NO: 4, or hybridize under high stringency conditions with SEQ ID NO: 2 or SEQ ID NO: 4, or gene molecules that belong to families highly homologous to the nucleotide sequences above. The nucleotide sequence encoding the polypeptides described may be the same as the coding region sequence shown in SEQ ID NO: 2 or SEQ ID NO: 4, or a fragment thereof, or a variant thereof that encodes the polypeptides but having different nucleotide at some sites. "Degenerate variant" refers to nucleotide sequences that encode amino acid sequences including SEQ ID NO: 1 or SEQ ID NO: 3, but has degeneracy compared with nucleotide sequences of SEQ ID NO: 2 or SEQ ID NO: 42.

Coding sequences for the polypeptides could be sequences encoding mature polypeptides, sequences encoding mature polypeptides and various additional coding sequences, sequences encoding mature polypeptides (and optionally additional coding sequences) and non-coding sequences.

The coding sequence for the polypeptides or the fragments thereof may be obtained by PCR, recombinant technology or artificial synthesis. With regards to PCR, the genome may be obtained from original microbes, such as *Thielavia terrestris, Lasiodiplodia theobromae*, then probes could be designed according to the nucleotide sequence of the polynucleotides described, to amplify lipase genes from the Genome DNA.

Also described are fragments of the polynucleotides above, the fragments often comprise 10 to 40, or preferably 15 to 30 bases, and could be used as primers or probes. "Fragment" herein refers to a continuous part of the coding sequence.

Nucleic Acid Construct

A nucleic acid construct, which may be single-stranded or double stranded, may contain the coding sequence of the polynucleotides and operably links with one or more control sequence such that the control sequences direct the expression of the coding sequence in host cells under suitable conditions to provide the polypeptides of SEQ ID No. 1 or 3. The polynucleotides or coding sequences may be modified in various way to guarantee the expression of the polypeptides. Modification of the polynucleotides before being inserted to the nucleic acid construct may be needed or necessary according to the features of the expression plasmids or vectors. The nucleotide sequence may be modified by using recombinant DNA technology.

Control sequence may be suitable promoters, which are nucleotide sequences that are used for the expression of the polynucleotides into the polypeptides and that are recognized by host cells. The control sequence may also be a coding region of terminators which link with the 3' end of the polynucleotide. Any terminator that functions in a selected host cell may be used. The control sequence may also be a coding region for a suitable leader peptide or leading peptide, which links to the 5' end of the polynucleotide. Any leader peptide that functions in the selected host cell may be used. The control sequence may be a coding region for signal peptides which link to the amino acid end of the polypeptides and direct the polypeptides into secretion approaches of the host cells. Various control sequences for gene manipulation and protein expression, and their use in the recombinant expression of lipase genes is known.

Clone vectors or expression vectors containing the polynucleotide of SEQ ID No. 2 or 4 may also be used. These vectors may contain control sequences mentioned above as well.

Expression plasmids or expression vectors could be any vectors, such as plasmid or virus, which may be manipulated by recombinant DNA technology to result in the expression of the nucleotide sequence of interests. A vector could be chosen according to the compatibility of the vector with the host cell which would be transformed with the vector. The vectors could be linear or closed circular vectors. The expression vector preferably contains components that allow the vector to integrate into the host cell genome or allow the vector to autonomously replicate independent to the genome in the host cell.

The expression vectors may contain one or more selectable markers that permit easy transformation, transfection, transduction and the like. The selectable markers are gene sequences, which provide host cells resistance to antibiotics or virus, resistance to heavy metals, changes from protorophic to auxotrophic, and so on.

The expression vectors may contain an artificial sequence, which contains multiple restriction endonuclease recognition sites, providing a variety of insertable sites and solutions for foreign DNA. The expression vectors may contain a sequence encoding peptides, such as 6His, that facilitate extraction and purification of the protein.

More than one copy of the polynucleotide may be inserted into a host cell to increase the yield of the product of the polynucleotide. The increase in the copy number of the polynucleotide may be achieved by integrating at least one additional copy of the sequence into the host cell genome or by including an amplifiable selectable marker gene and the polynucleotide, and the cell comprising an additional copy of polynucleotide could be screened by culturing the cell in the presence of a suitable selection agent.

In some embodiments, the expression vector may be used to express the polypeptide in *Escherichia coli* (*E. coli*). Hence, in some embodiments, the expression vector contains promoter AOX1, signal peptide α-Factor, expression frame His4, terminator AOX1, and/or multiple cloning sites. Preferably, the nucleic acid construct or the expression vector has a pPIC9K plasmid as the backbone.

Recombinant Host Cells

A recombinant host cell containing the polynucleotide of the present invention for the production of the polypeptide may be used. Vectors containing the polynucleotide is directed into host cells so that the vector becomes a component of the chromosome or self-replicates autonomously as explained earlier. The host cell is chosen depending largely on the gene encoding the polypeptide and its origin.

The host cell may be a plant cell, a single cell microorganism or a non-single cell microorganism. Single cell microorganisms can be, such as Gram-positive bacteria, including but not limited to *Bacillus*, for example, *Bacillus alkalophilus, Bacillus amyloliquefaciens, Bacillus brevis, Bacillus megaterium, Bacillus subtilis, Bacillus lichenifor-* *mis, Bacillus coagulans, Bacillus stearothermophilus* and *Bacillus thuringiensis;* or *Streptomyces,* such as *Streptomyces lividans;* or Gram-negative bacteria, such as *Escherichia coli* and *Pseudomonas.* Preferably, the bacterial host cell is *Bacillus subtilis, Bacillus licheniformis, Bacillus stearothermophilus* or *E. coli.*

The host cell of the present invention may be a eukaryote, such as a mammalian, insect, plant, yeast or fungal cell. Preferably, the host cell is a fungal cell. As used herein, "fungi" or "fungal" includes Ascomycota, Basidiomycota, Chytridiomycota, Zygomycota, and Oomycete.

Alternatively, the host cell may be a prokaryotic cell. As used herein, "Prokaryotic cells" include cells of *Pseudomonas, Bacillus, Enterobacter, Staphylococcus, Streptomyces,* and *Escherichia.* The host cell may be a cell of *Pseudomonas, Bacillus, Streptomyces,* and *Escherichia.* Examples include *Bacillus subtilis, Pseudomonas fluorescens, Pichia pastoris, Escherichia coli,* and *Streptomyces lividans* and so on. Preferably, the host cell is a cell of *Escherichia coli* or *Pichia pastoris.*

A nucleic acid construct comprising a polynucleotide sequence of SEQ ID No. 2 or 4 may be transformed into a host cell by conventional transfection or transformation methods. Transfection methods usually includes transient transfection and stable transfection. Techniques for transfection include chemical transfection, such as the DEAE-dextran method, the calcium phosphate method, and the artificial liposome method, and physical transfection, such as microinjection, electroporation, and gene guns.

Applications

The polypeptide of SEQ ID No. 1 or 3 may be applied in food industry, pharmaceutical industry, chemical industry, and so on. Specifically, the polypeptides may be used in the hydrolysis of oil or fat and the transesterification or esterification reactions to produce fatty acid methyl/ethyl esters. The polypeptide may be used in the hydrolysis of milk fat in dairy products, to enhance the flavor of cheese, milk powder, and cream, to promote the ripening of cheese, and to improve the quality of dairy products; be used in dough, to improve the elasticity of the product, the sense of the food, and the freshness of bread, etc. The polypeptide may be used in the hydrolysis of fatty acid methyl esters in the chemical industry, such as methyl octanoate or methyl decanoate, for the production of fatty acids; be added to detergents for removing oil stains, general cleaning, bleaching, etc.; be used in the cleaning of industrial waste or degradation of organic waste; be added to various substrates for the production of fatty acid methyl/ethyl esters, i.e. biodiesel, and so on.

The polypeptides may be used in the hydrolysis of fatty acid methyl esters, for example the hydrolysis of medium and short chain fatty acid methyl esters, especially fatty acid methyl esters containing C4~C12 chain fatty acid, most preferably the hydrolysis of methyl octanoate or methyl decanoate. The amount of the polypeptide of the present invention used in various fields mentioned above could be determined conventionally, preferably in the range of 60 to 200 microgram per gram of oil, or more preferably 80 to 120 microgram per gram of oil.

The polypeptides may be used in the production of biodiesel, for example the conversion of palm free fatty acid distillate (PFAD), mixed vegetable acid oil, used cooking oil, tallow, crude palm oil, vegetable oils into fatty acid methyl esters or fatty acid ethyl esters. The amount of the polypeptide used may be at least 20 ppm, preferably at least 50 ppm.

The polypeptides, coding sequences or polynucleotides, nucleic acid constructs, and cells may be used in the food industry, medical and health industry, chemical industry, and so on. Particularly, the polypeptide, coding sequence or polynucleotide, nucleic acid construct, and cell may be used in the hydrolysis of fatty acid esters, such as fatty acid methyl esters containing C4~C12 chain, especially methyl octanoate or methyl decanoate. Particularly, the polypeptide, coding sequence or polynucleotide, nucleic acid construct, and cell may be used in the transesterification or esterification reactions to obtain fatty acid methyl/ethyl esters for the production of biodiesel, for example the substrates could be palm free fatty acid distillate (PFAD), mixed vegetable acid oil, used cooking oil, tallow, crude palm oil, vegetable oils, etc.

In an example, a composition contains a fatty acid methyl ester, water, a polypeptide, or cells which produce the polypeptide, or cells containing the polynucleotide encoding the polypeptide. The fatty acid methyl ester may be methyl octanoate or methyl decanoate and may be hydrolysed by the polypeptide to produce the fatty acid. The amount of the polypeptide used in the hydrolysis of fatty acid methyl ester may be at least 30 ppm, preferably at least 40 ppm.

In another example, a composition, contains oils or PFAD, an alcohol, in particular a C1-C4 alcohol like methanol or ethanol, and a polypeptide, or cells which produce the polypeptide, or cells containing a polynucleotide encoding the polypeptide may be provided. The polypeptide may cause esterification or transesterification of the fatty acid to provide the ester which may be used in as a biodiesel. The amount of the polypeptide used in the conversion of free fatty acid or triglyceride into fatty acid methyl/ethyl ester may be at least 20 ppm, preferably at least 50 ppm. The weight amount of water used is 3 to 12% of the weight of the oil, preferably 4 to 8%, more preferably 4-6%

The polypeptide may be provided in the form of a pure enzyme preparation or in the form of a composition. Said composition could be a powder composition, a liquid composition, or a paste composition. When provided in the form of a composition, the composition may contain different excipients depending on the use of the composition. Excipients may be added to the composition of the present invention, including but not limited to one or more of following stabilizer or other components: sorbitol, potassium sorbate, methyl benzoate, ethyl benzoate, sucrose, mannose, trehalose, starch, sodium chloride, calcium chloride, etc.

A process for performing oil refining, oleochemical reaction, improvement for feeds, food preparation, medicine preparation, wherein the process is conducted under the following conditions: a) temperature between 20° C. to 70° C., preferably 30° C. to 50° C., more preferably 35° C. to 45° C. or 40° C. to 50° C., and/or, b) pH between 3 to 9, preferably between 5.5 to 9.0, preferably 6.5 to 7.5, and/or, c) an amount of polypeptide and water.

Experimental methods which are not specified in the following examples are either carried out according to the conditions recommended by the manufacturers or in accordance with conventional methods or conditions, such as specified in Sambrook et al., Molecular Cloning: A laboratory Guide (Cold Spring Harbor Laboratory Press, 1989). With regard to usages and amounts of reagents, unless otherwise stated, conventional usage and dosage are applied. Unless otherwise stated, percentages refer to weight percentages.

EXAMPLES

The source of the materials used in the following examples are sourced from the companies and/or brands mentioned in the brackets. The name of the companies and/or may be registered trademarks including Invitrogen®, New England Biolabs®, Sigma-Aldrich®, Alfa Aesar®, Merck®, Fisher®, and VWR®.

Materials and Experimental Methods

Strains and Plasmids:

Strains: *Pichia pastoris* GS115 (Invitrogen®, product No. C181-00), *Escherichia coli* DH5-alpha (New England Biolabs®, Catalog #C2987I)

Plasmid: pPIC9K (Invitrogen®, product No. V175-20)

Mediums and solutions:

LB: 10 g/L tryptone (Sigma Aldrich®), 5 g/L yeast extract (Sigma Aldrich®), 10 g/L Sodium Chloride (Sigma Aldrich®)

LB agar medium: 10 g/L tryptone (Sigma Aldrich®), 5 g/L yeast extract (Sigma Aldrich®), 10 g/L Sodium Chloride (Sigma Aldrich®), 20 g/L Bactoagar (Sigma Aldrich®)

YPD: 20 g/L peptone (Sigma Aldrich®), 20 g/L D-glucose (Sigma Aldrich®), 10 g/L yeast extract (Sigma Aldrich®)

YPD agar medium: 20 g/L peptone (Sigma Aldrich®), 20 g/L D-glucose (Sigma Aldrich®), 10 g/L yeast extract (Sigma Aldrich®), 20 g/L Bactoagar (Sigma Aldrich®)

RDB agar medium (hereinafter, RDB): 1M sorbitol (Sigma Aldrich®), 20 g/L D-glucose (Sigma Aldrich®), 34 g/L yeast nitrogen base without ammonium sulphate and amino acid (Sigma Aldrich®), 100 g/L ammonium sulphate (Alfar Aesar®), 0.4 mg/L biotin (Sigma Aldrich®), 20 g/L bactoagar (Sigma Aldrich®), 50 mg/L L-glutamic acid (Sigma Aldrich®), 50 mg/L L-methionine (Sigma Aldrich®), 50 mg/L L-lysine (Sigma Aldrich®), 50 mg/L L-leucine (Sigma Aldrich®), 50 mg/L L-isoleucine (Sigma Aldrich®)

BMGY: 0.1 M potassium phosphate buffer, pH 6.0 (Merck®), 34 g/L yeast nitrogen base without ammonium sulphate and amino acid (Sigma Aldrich®), 10 g/L yeast extract (Sigma Aldrich®), 20 g/L peptone (Sigma Aldrich®), 100 g/L ammonium sulphate (Alfar Aesar®), 0.4 mg/L biotin (Sigma Aldrich®), 1% v/v glycerol (Fisher®)

BMGY agar medium: 0.1 M potassium phosphate buffer, pH 6.0 (Merck®), 34 g/L yeast nitrogen base without ammonium sulphate and amino acid (Sigma Aldrich®), 10 g/L yeast extract (Sigma Aldrich®), 20 g/L peptone (Sigma Aldrich®), 100 g/L ammonium sulphate (Alfar Aesar®), 0.4 mg/L biotin (Sigma Aldrich®), 1% v/v glycerol (Fisher®), 20 g/L bactoagar (Sigma Aldrich®)

BMMY: 0.1 M potassium phosphate buffer, pH 6.0 (Merck®), 34 g/L yeast nitrogen base without ammonium sulphate and amino acid (Sigma Aldrich®), 10 g/L yeast extract (Sigma Aldrich®), 20 g/L peptone (Sigma Aldrich®), 100 g/L ammonium sulphate (Alfar Aesar®), 0.4 mg/L biotin (Sigma Aldrich®), 1% v/v methanol (Merck®)

BMMY agar medium: 0.1 M potassium phosphate buffer, pH 6.0 (Merck®), 34 g/L yeast nitrogen base without ammonium sulphate and amino acid (Sigma Aldrich®), 10 g/L yeast extract (Sigma Aldrich®), 20 g/L peptone (Sigma Aldrich®), 100 g/L ammonium sulphate (Alfar Aesar®), 0.4 mg/L biotin (Sigma Aldrich®), 1% v/v methanol (Merck®), 20 g/L bactoagar (Sigma Aldrich®)

Fermentation Basal Salt Medium: 26.7 mL/L 85% phosphoric acid (Alfar Aesar®), 0.93 g/L calcium sulphate (Alfar Aesar®), 18.2 g/L potassium sulphate (Sigma Aldrich®), 14.9 g/L magnesium sulphate heptahydrate (Merck®), 4.13 g/L potassium hydroxide (Sigma Aldrich®), 40 g/L glycerol (VWR)

PTM Trace Salts: 6 g/L copper (II) sulphate (Sigma Aldrich®), 80 mg/L sodium iodide (Sigma Aldrich®), 3 g/L manganese sulphate monohydrate (Sigma Aldrich®), 200 mg/L sodium molybdate dihydrate (Sigma Aldrich®), 20 mg/L boric acid (Sigma Aldrich®), 500 mg/L cobalt chloride (Sigma Aldrich®), 20 g/L zinc chloride (Sigma Aldrich®), 65 g/L iron (II) sulphate heptahydrate (Merck®), 200 mg/L biotin, 5 mL/L sulphuric acid (Sigma Aldrich®)

The origin of restriction endonuclease NotI, EcoRI, SalI and SnaB1 were purchased form New England Biolabs, via Axil Scientific Singapore. PCR polymerase KOD Hot Start DNA Polymerase was purchased from Merck Singapore. DNA ligase T4 DNA ligase and HiFi DNA Assembly were purchased from New England Biolabs, via Axil Scientific Singapore. Commercial lipases *Thermomyces lanuginosa* lipase (TLL), Eversa® Trans 2.0, *Candida antartica* lipase B (CalB) were purchased from Sigma Aldrich®.

Definition for enzyme activity: Unit (U) of lipase activity in the hydrolysis reaction corresponds to amount of enzyme which liberates 1 μmol of free fatty acid per minute under the test conditions.

To calculate hydrolytic lipase activity: Units/mL enzyme= (Volume of NaOH titrated (mL)×Molarity of NaOH (M) used×Time (min)×Dilution factor of enzyme used×1000)/Volume of enzyme used (mL)

Unit (U) of lipase activity in the production of biodiesel, via esterification, corresponds to one micromole of free fatty acid consumed per minute under the given experimental conditions.

Example 1: Construction of Recombinant pPIC9K Plasmids

Figure 9:
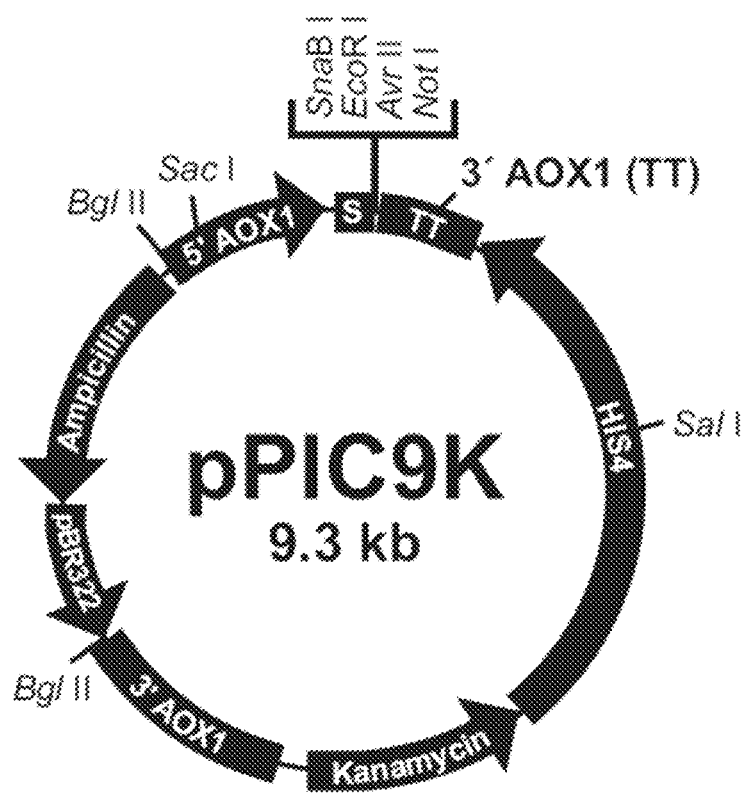
FIG. 9 shows a restriction map of a pPIC9K plasmid.

Construction of P9K-TTL: Polynucleotide of TTL (SEQ ID NO.:2) was synthesized by Bio Basic Asia Pacific® and cloned in frame to alpha factor secretion in commercially available pPIC9K vector via restriction endonuclease recognition EcorI and AvrII to obtain the recombinant plasmid P9K-TTL. Expression of the gene is driven by the AOX1 promoter and terminated by the AOX1 terminator. FIG. 9 shows an example of a pPIC9K plasmid that may be used.

Construction of P9K-LTL3: Polynucleotide of LTL3 (SEQ ID NO.:4) was synthesized by Bio Basic Asia Pacific® and cloned in frame to alpha factor secretion in commercially available pPIC9K vector with Gibson Assembly via SnaB1 restriction digestion site to obtain the recombinant plasmid P9K-LTL3. Expression of the gene is driven by the AOX1 promoter and terminated by the AOX1 terminator. FIG. 9 shows an example of a pPIC9K plasmid that may be used.

Example 2: Construction and Selection of Recombinant Strains

Competent cells of *Pichia pastoris* GS115 strain were prepared according to the protocol described by Wu et al (Wu S. and Letchworth G. J., Biotechniques, Vol. 36, No. 1, 2018, DOI:10.2144/04361DD02). 8×108 cells were resuspended in 100 mM LiAc, 10 mM DTT, 0.6 M sorbitol and 10 mM Tris-HCl, pH 7.5 for 30 min. Cells were washed with 1 M sorbitol and resuspended in 1 M ice-cold sorbitol to final concentration of 1010 cells/mL. 300 ng of P9K-LTL3 and P9K-TTL respectively were used to transform *Pichia pastoris* GS115. The transformation was carried out as previously described by Wu et al.

Figure 1B:
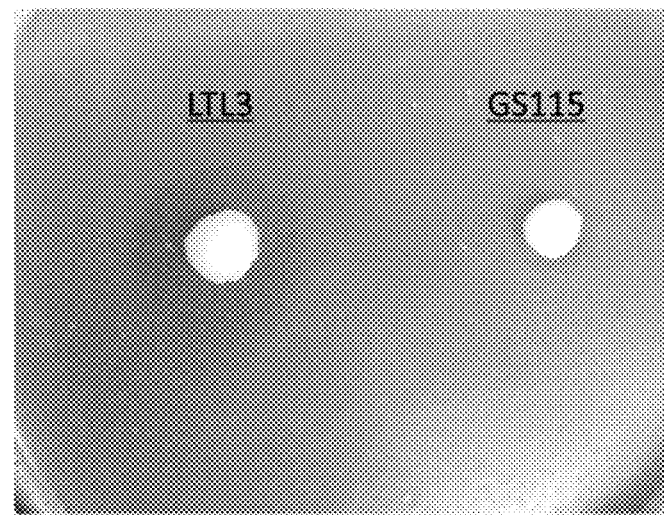
FIG. 1B shows the comparison of positive transformant GS115(P9K-LTL3) on the left (marked as "LTL3") with the control GS115 without being transformed vectors on the right. The halo circle around the positive transformant GS115(P9K-LTL3) shows the recombinant strain has lipase activity.

The transformants were spread on RDB and cultivated under 30° C. for 4 days. Positive clones were transferred to BMGY agar and cultivated under 30° C. for 1 day. Clones were then transferred to BMMY agar supplemented with 1% tributyrin (for GS115 (P9K-TTL)), and 2% tributyrin (GS115 (P9K-LTL3)) for induction with GS115 strains as the control, for 4 days to obtain plates as shown in Figures: FIG. 1A shows the comparison of positive transformant GS115 (P9K-TTL) on the left with the control GS115 on the right; FIG. 1B shows the comparison of positive transformant GS115 (P9K-LTL3) on the left with the control GS115 on the right.

Example 3: Recombinant Expression of Lipase in GS115 and Initial Test of Enzyme Activity For TTL (SEQ ID No. 1) and LTL3 (SEQ ID No. 3) lipase expression by fermentation, GS115(P9K-TTL) and GS115 (P9K-LTL3) were first precultured in BMGY liquid media at 30° C., 220 rpm, overnight in shake flasks at 20% flask volume. After reaching an OD600 of between 2 to 6, fermentation was carried out according to the suggested protocol by Invitrogen®, Life Technologies. Fermentation was carried out in a fermentation basal salt medium supplemented with 4.35 mL/L PTM trace salts, with initial settings of 30° C., pH 5.0, 1500 rpm, 1 L/L/min (or 1 vvm, vessel volume per minute). The glycerol batch phase was first carried out over 20 to 24 hours, where dissolved oxygen levels were kept above 20%, until wet cell mass of 90 to 150 g/L was achieved. Second, in the glycerol fed-batch phase, a constant rate of 18.15 mL/L/h of 50% v/v glycerol supplemented with 12 mL/L PTM trace salts was fed into the flask for about 4 hours, until wet cell mass of 180 to 220 g/L was achieved. Finally, to induce protein expression via AOX1 promotor on pPIC9K plasmid, methanol supplemented with 12 mL/L PTM trace salt was fed in an incremental manner. For the first four hours, feed rate was set at 3.6 mL/L/h. Following next two hours, feed rate was increased to 7.3 mL/L/h. A final feed rate was set at 10.9 mL/L/h until the end of fermentation. The culture supernatant containing secreted TTL lipase was harvested by centrifugation at 14 000 rpm, for 20 min, and filtered with a 0.22 μm membrane (Nalgene®).

Activity of secreted lipase harvested from culture supernatant were calculated as shown below. Unit (U) of lipase activity corresponds to amount of enzyme which liberates 1 μmol of free fatty acid per minute under the test conditions.

GS115 (P9K-TTL): 400 ml of TTL (SEQ ID No. 1) at a protein concentration of (0.616 mg/ml) was obtained by fermentation in a 1 L bioreactor. 10 μl of crude supernatant was reacted with 390 μl of water and 50 μl of vinyl-laurate as substrate at 37° C. for 15 min at 2000 rpm. 2.12 ml of 50 mM NaOH was required to neutralize the free fatty acid liberated (control: 0.4 ml). Hence, the unit activity of TTL on vinyl laurate was determined to be 920 U/ml.

GS115(P9K-LTL3): Total protein yield of 0.551 mg/mL was obtained by fermentation in a 1 L bioreactor. Reacting 2 μL of crude LTL3 (SEQ ID No. 3), with 138 μL water, 40 μL 200 mM Tris-HCl pH 7.2 buffer and 120 μL of substrate (tributyrin, vinyl laurate or olive oil) in a 2 mL tube (Eppendorf®), at 37° C., 2000 rpm, for 30 min. Free fatty acids liberated were neutralized with 50 mM NaOH and unit activities were calculated to be 333, 3833 and 133 U/mL respectively. A reaction mixture without enzyme added was used as control. Protein concentration was measured with Bradford reagent (Sigma Aldrich®) with bovine serum albumin (Sigma Aldrich®) as standards.

Example 4: Characterization of Lipases

1. Substrate Specificity of TTL (SEQ ID No. 1)

Figure 2:
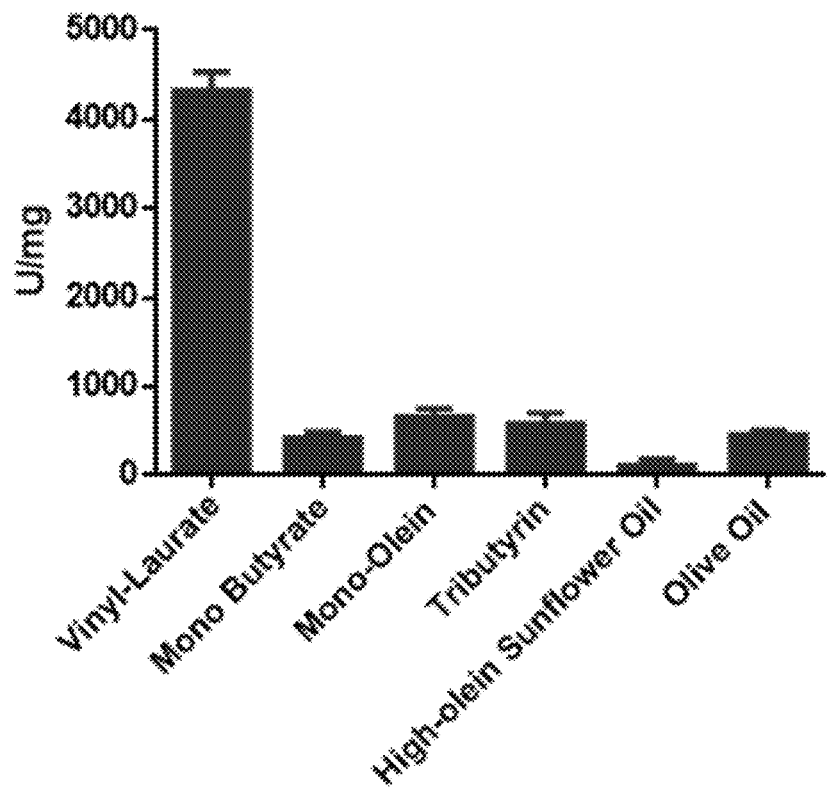
FIG. 2 shows the substrate specificity of TTL. The initial hydrolysis activity of TTL was tested with tributyrin, higholein sunflower oil, olive oil, vinyl laurate, monobutyrin and monoolein.

GS115 (P9K-TTL): Hydrolysis was performed using 1 μL of TTL prepared in Example 3, 399 μL phosphate-buffered saline (PBS) and 50 μL of substrate in a 1.5 mL Eppendorf® tubes. The reaction was performed at 37° C. for 15 min on a thermomixer at 2000 rpm. Unit activity of TTL for different substrates are shown in FIG. 2: vinyl-laurate (4322±214U), mono butyrate (422±69U), mono olein (656±102U), tributyrin (577±126U), high-oleic sunflower oil (111±69U) and olive oil (456±51U).

2. Optimum Temperature of TTL (SEQ ID No. 1)

Figure 3:
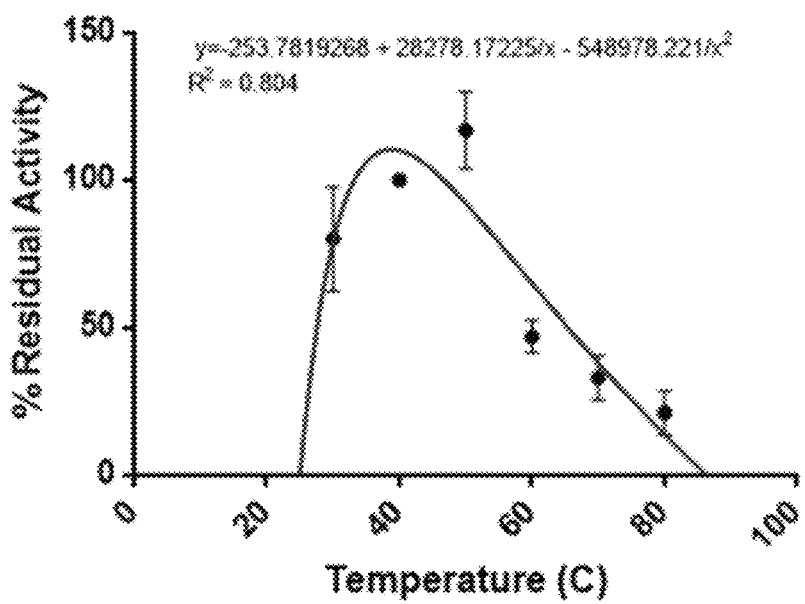
FIG. 3 shows the activity of TTL between 25° C. to 90° C.

GS115 (P9K-TTL): Hydrolysis was performed using 1 μL of TTL, 399 μL phosphate-buffered saline (PBS) and 50 μL of substrate in a 1.5 mL Eppendorf® tubes. The reaction was performed at temperatures ranging from 30-80° C. for 15 min on a thermomixer at 2000 rpm. Residual activity is then calculated by normalizing the activity of the enzyme at the indicated temperature to the activity of the enzyme at 37° C. TTL has an optimal temperature of 50° C. (as shown in FIG. 3).

3. Optimum pH of TTL (SEQ ID No. 1)

Figure 4:
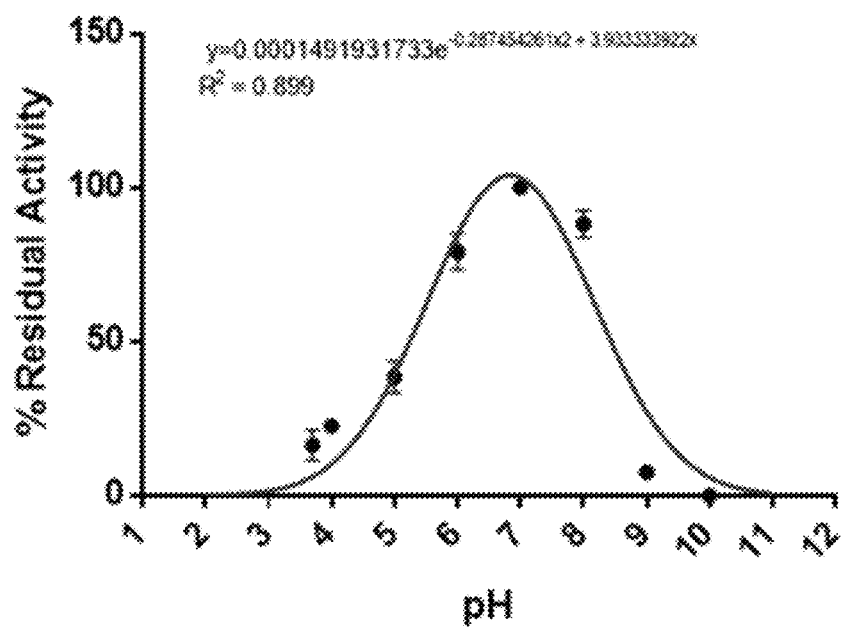
FIG. 4 shows the initial hydrolysis activity of TTL in different pH conditions ranging from 3.7 to 10.0.

GS115 (P9K-TTL): Hydrolysis was performed using 1 μL of TTL, 399 μL of buffers of pH ranging from (3-10) and 50 μL of substrate in a 1.5 mL Eppendorf® tubes. The reaction was performed at 37° C. for 15 min on a thermomixer at 2000 rpm. Residual activity is then calculated by normalizing the activity of the enzyme at the indicated pH to the activity of the enzyme at pH 7.0. TTL has an optimal pH range of 6 to 8, with an optimal value of 7 (shown in FIG. 4).

4. Substrate Specificity of LTL3 (SEQ ID No. 3)

Figure 5:
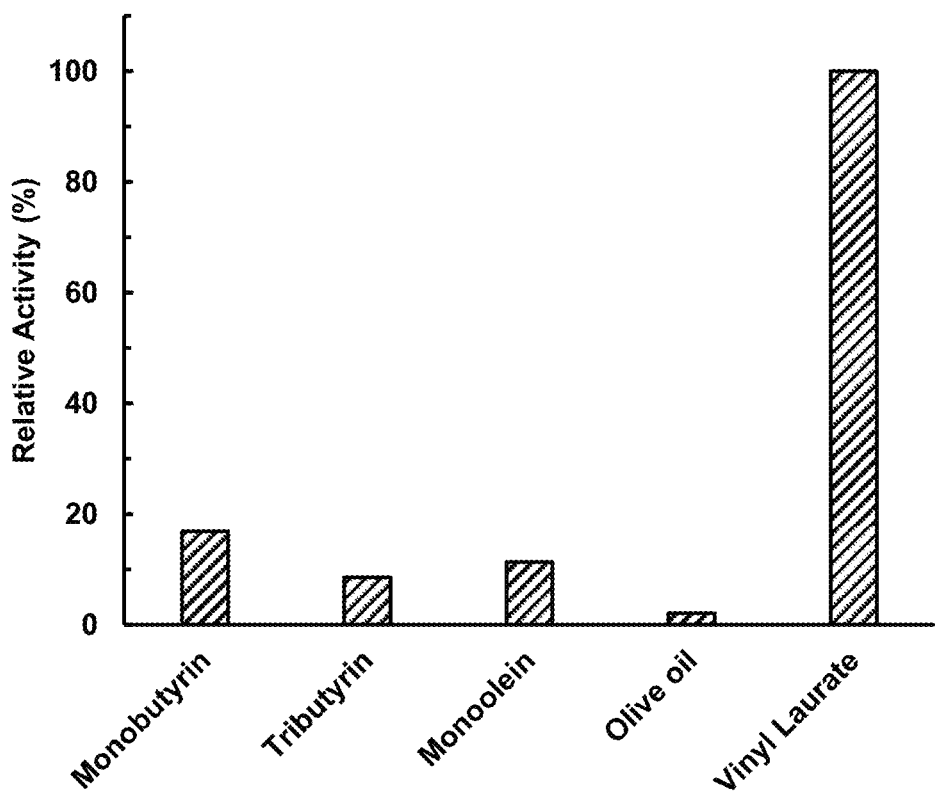
FIG. 5 shows the substrate specificity of LTL3. The initial hydrolysis activity of LTL3 was tested with tributyrin, coconut oil, vinyl laurate and olive oil.

GS115 (P9K-LTL3): Hydrolysis was performed using 2 μL of LTL3, 138 μL water, 40 μL 0.2 M Tris-HCl buffer (pH 7.2) and 120 μL of different substrates in a 2 mL Eppendorf® tube. The reaction was performed at 37° C. for 15 min on a thermomixer (Eppendorf®) at 2000 rpm. Unit activity of LTL3 for different substrates are shown in FIG. 5: 494 U/mg for tributyrin, 5807 U/mg for vinyl laurate, 181 U/mg for coconut oil and 121 U/mg for olive oil. It may be seen that LTL3 is selective for medium chain fatty esters and acids like vinyl laurate compared to short chain (C4-C6 fatty acids) like butyrate ester and long chain (greater than 14 carbon atoms) like monoolein ester and olive oil which is mainy up of oleic (C18) and palmitic (C16) acids and esters. LTL3 may also be selective for monoester over triglycerides or diacylglycerides.

5. Optimum Temperature of LTL3 (SEQ ID No. 3)

Figure 6:
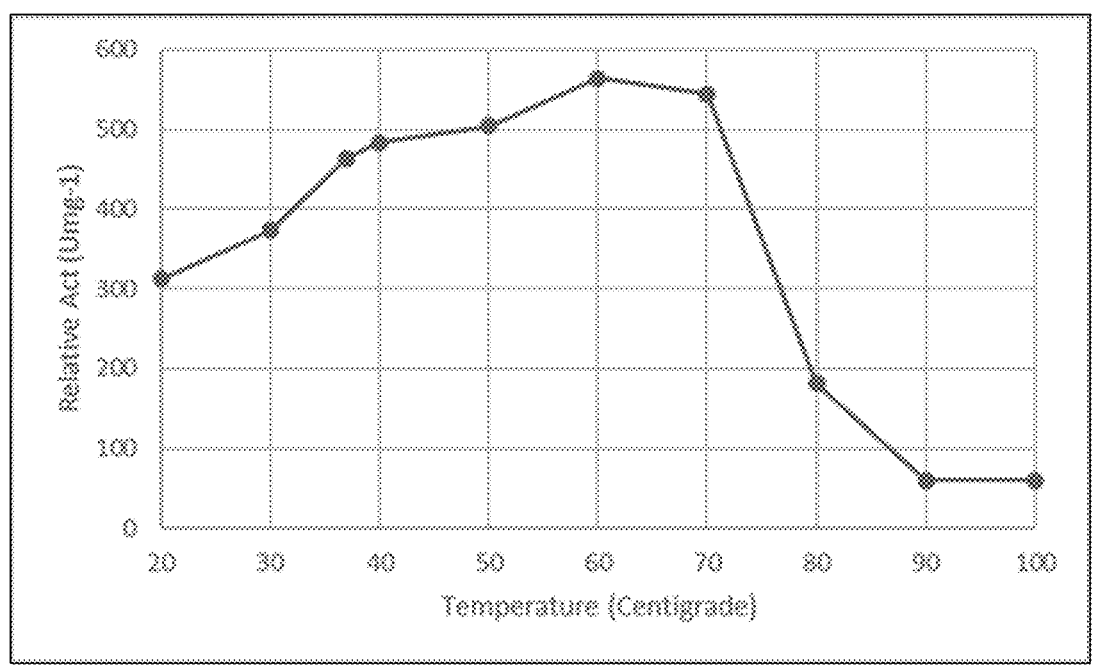
FIG. 6 shows the activity of LTL3 between 20° C. to 100° C.

GS115 (P9K-LTL3): Hydrolysis was performed using 2 μL of LTL3, 138 μL water, 40 μL 0.2 M sodium citrate-citric acid buffer (pH 6.0) and 120 μL of tributyrin in a 2 mL Eppendorf® tubes. The reaction was performed at temperatures ranging from 20 to 100° C. for 15 min on a thermomixer (Eppendorf®) at 2000 rpm. Free fatty acid liberated was neutralized with 50 mM NaOH. It may be observed from FIG. 6 that LTL3 shows enzymatic activity of at least 300 U mg$^{-1}$ in the temperature range of 20 to 70° C. The temperature range of 37 to 70° C. showed greater enzymatic activity, in particular at the temperatures of 60 to 70° C.

6. Optimum pH of LTL3 (SEQ ID No. 3)

GS115 (P9K-LTL3): Hydrolysis was performed using 2 μL of LTL3, 138 μL water, 40 of different 0.2 M buffers ranging from pH 3.0 to 10.0 and 120 μL of tributyrin in a 2 mL Eppendorf® tubes. The reaction was performed at 37° C. for 15 mins on a thermomixer (Eppendorf®) at 2000 rpm. Free fatty acid liberated was neutralized with 50 mM NaOH.

Figure 7:
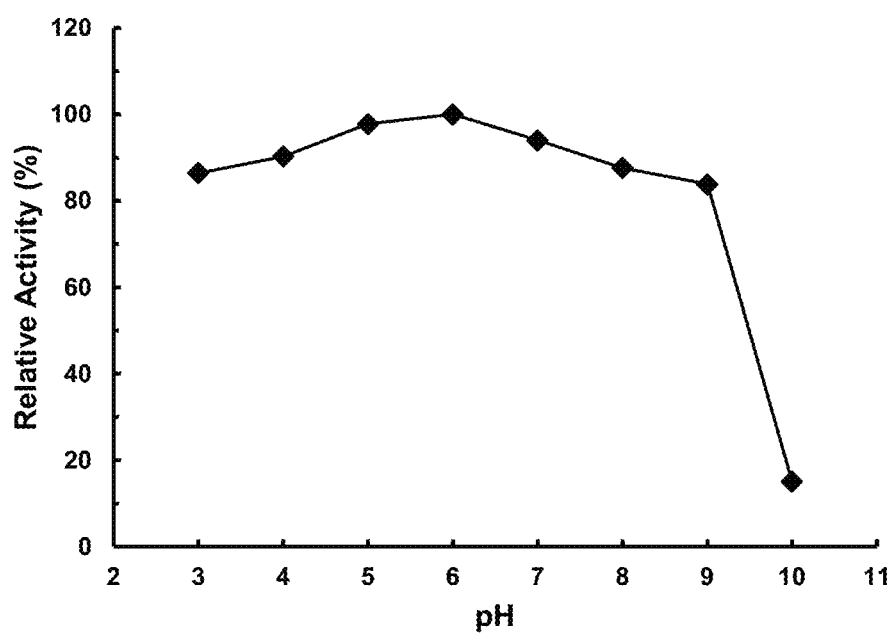
FIG. 7 shows the initial hydrolysis activity of LTL3 in different pH conditions ranging from 3 to 10.

From FIG. 7, it may be observed that LTL3 operates with high activity in a pH of 3 to 9, in particular LTL3 was particularly active at a pH of 5 to 6.

Example 5: Hydrolysis of C8C10 Methyl Ester by TTL (SEQ ID No. 1) and LTL3 (SEQ ID No. 3)

The TTL hydrolysis of C8C10 methyl ester (a mixture of methyl octanoate and methyl decanoate with a product specification of 50-58% of C8 methyl ester and 35-50% of C10 methyl ester), purchased from Wilmar Oleochemicals Co., Ltd®, China) was performed as follows: 4 mL (3.53 g) of C8C10 methyl ester was reacted with 480 μg (mass of the solid enzyme) or 136 ppm (mass of the solid enzyme with respect to the mass of methyl ester) of TTL enzyme (from Example 3) in 16 mL of water in a 50 mL opened round bottom flask.

A reaction temperature of 40° C. was maintained by a heated plate, and a magnetic stirrer was used for agitation at 400 rpm. After 88 hours, the hydrolysis rate of C8C10 methyl ester is calculated according to the calculation method shown below to be 98.4%.

Hydrolysis of C8C10 methyl ester by LTL3 was performed by reacting 4 mL (3.53 g) of C8C10 methyl ester substrate with 8 mL of water, and 600 μg or 170 ppm (mass of the solid enzyme with respect to the weight of methyl ester) of LTL3 enzyme (from Example 3) in a 25 mL opened round bottom flask at 40° C. Reaction was carried out on a heated plate, at 400 rpm agitation. After the required time, the mixture was spun at 4000 rpm for 20 min to allow phase separation into a light phase and a heavy phase. The light phase contained the desired product (C8 and C10 free fatty acids) and trace amount of methanol. The heavy phase contained water, enzyme and trace amount of methanol. The light phase was collected and subjected to vacuum evaporation (for example using a rotary evaporator) to remove the residual methanol.

For the enzyme, the percentage value is the volume of liquid enzyme solution to the weight of the oil. The enzyme dosage in ppm is the mass of the enzyme protein relative to the mass of the oil (or substrated).

After 24 and 48 hours, the hydrolysis rate of C8C10 methyl ester is calculated according to the calculation method shown below to be 85% and 95% respectively. A hydrolysis yield of at least 90% (i.e. 90% conversion) is preferred as the product is of sufficient purity to require minimal or no additional processing, in particular distillation which may not be cost effective. A hydrolysis yield of 95% may provide a product that may be of a commercial grade, i.e. the product can be sold without additional processing. An acid value of about 320 corresponds roughly to 90% hydrolysis of the ester.

$$\% \text{ Hydrolysis} = (AV - AV_0)/(SV - AV_0)$$

The Hydrolysis rate was calculated by dividing the acid value after the reaction with the saponification value (SV) of 357. AV: Acid value of the hydrolysis product, $AV_0$: Initial acid value of 0.26. The acid value was determined by titrating the light phase product obtained after centrifuging and drying.

Another set of experiments was performed using 20 g of C8C10 methyl ester, 40 g of water, and different concentration of LTL3 at a reaction temperature of 45° C., 500 rpm stirring, and a vacuum pressure of 50-55 mbar was applied continuously to remove the methanol produced. The product was obtained via centrifugation and drying as above. With a LTL3 concentration of 44 ppm (mass of the solid enzyme with respect to the weight of methyl ester), hydrolysis rates of 88.0% and 95.3% were obtained after 24 h and 48 h respectively. With 30 ppm of LTL3, hydrolysis rates of 73.9% (acid value of 264.71), 89.8% (acid value of 320.78) and 94.7% (acid value of 338.45) were obtained after 24 h, 48 h and 72 h respectively.

The results show that lipase TTL and LTL3 have good hydrolysis activity on the C8C10 methyl ester. In particular, LTL3 was able to perform the hydrolysis at a concentration as low as 30 ppm in a given reaction time to give the hydrolysis product of high purity. This provides substantially higher operational efficiencies in using low amounts of the enzyme and avoiding difficult purification and isolation of the product, in particular distillation which is energy intensive.

Example 6: Comparison of Enzyme Activity with Commercial Lipase

TABLE 1

Hydrolysis of C8C10 methyl-ester by Eversa (Novozyme) and LTL3

| Experiment | 1A | 1B | 1C | 1D | 1E | 1F |
|---|---|---|---|---|---|---|
| C8/C10-OMe (mL) | 1 | 1 | 1 | 1 | 1 | 1 |
| Water (mL) | 2 | 2 | 2 | 2 | 2 | 1 |
| Lipase | Eversa ® | Eversa ® | Eversa ® | Eversa ® | Eversa ® | LTL3 |
| Enzyme concentration (ppm relative to oil amount) | 17 | 34 | 68 | 170 | 340 | 170 |
| % Yield 24 h | 28.9 | 24.7 | 37.3 | 44.2 | 58.5 | 85 |
| % Yield 48 h | 37.07 | 29.31 | 47.41 | 63.79 | 72.84 | 95 |

Conditions: 40° C., 1000 rpm, opened cap reaction in 15 mL tubes in thermomixer (Eppendorf ®).

Table 1 shows a comparison of the hydrolysis using LTL3 with the commercially available Eversa lipase. From Table 1, it may be seen that the LTL3 lipase is more efficient, and a lower quantity of the LTL3 lipase is required to achieve a higher hydrolysis rate and yield.

Figure 10:
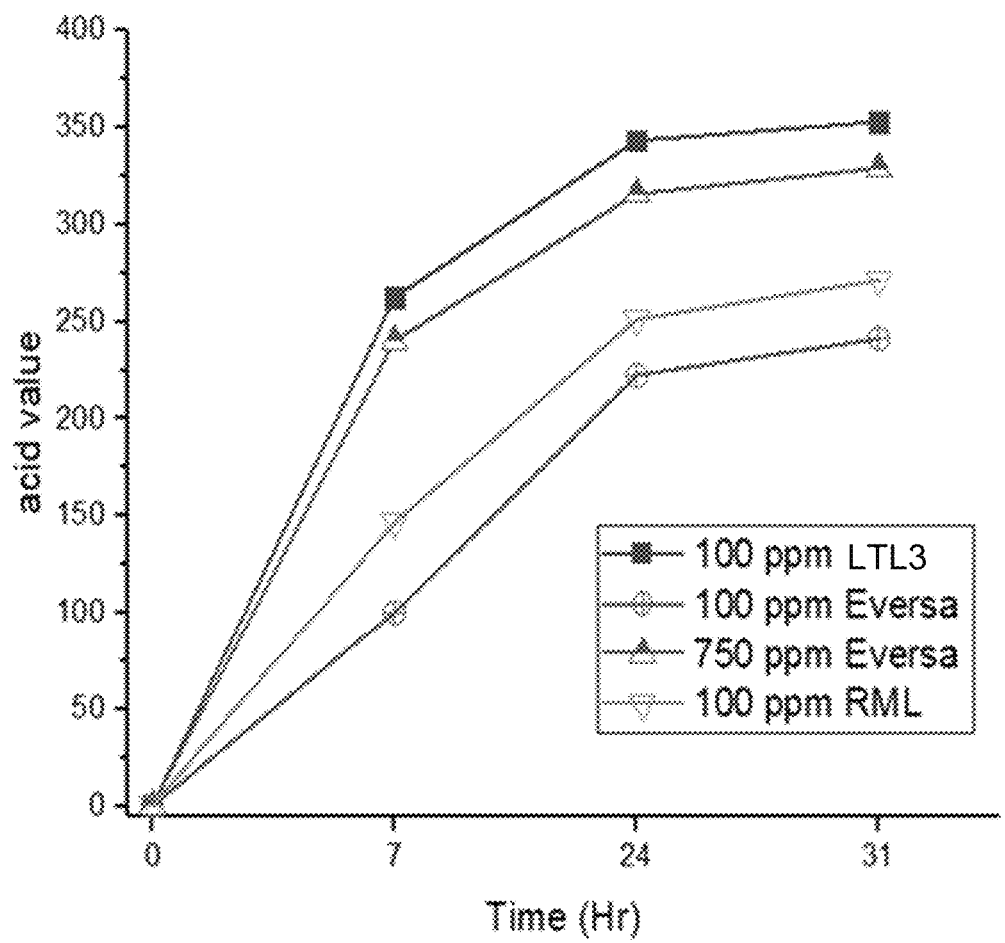
FIG. 10 shows a comparison of various enzymes for the hydrolysis of C8C10 ester.

FIG. 10 shows a comparison between the LTL3, Eversa and RML lipases (Novozymes®) for the hydrolysis of the C8C10 methyl ester. At 100 ppm (weight of the enzyme with respect to the weight of the ester), it is evident that LTL3 catalyses the hydrolysis more efficiently than both Eversa® and RML lipases at the same mass ratio at all time points. LTL3 produces a hydrolysis product with an acid value of 353.02 after 31 hours (hydrolysis rate 98.8%), which is higher than 100 ppm of RML and Eversa® which produced a hydrolysis product with an acid value of 271.34 (hydrolysis rate 75.9%) and 241.16 (hydrolysis rate 67.5%) respectively after 31 hours. The hydrolysis result obtained by using RML was 78% of the LTL3 sample; and the one obtained by Eversa® was 69% of the LTL3 sample. Even with 750 ppm of Eversa® (7.5 times the dosage of LTL3 used), the hydrolysis product had an acid value of 329.01 (hydrolysis rate 92.1%) after 31 hours which was lower than that obtained with LTL3.

The results show that LTL3 is more efficient than Eversa® and RML for hydrolysis of the C8C10 methyl ester. The capability of enzymatic hydrolysis of C8C10 methyl ester to achieve a higher hydrolysis rate, for example, more than 95%, in particular more than 98%, is crucial for industrial application, as such high hydrolysis rate can directly produce a hydrolysis product (C8C10 fatty acid), which directly meet the product specificity. This greatly simplifies the isolation and purification, in particular it may avoid a distillation step which is energy intensive, thereby the production cost can be significantly reduced.

Example 7: Hydrolysis of C8C10-Ester with LTL3 (SEQ ID No. 3) Under Low Pressure Conditions

TABLE 2

Hydrolysis of C8C10 methyl-ester under different pressure conditions

| | Experiment | | | |
|---|---|---|---|---|
| | 2A | 2B | 2C | 2D |
| Vacuum pressure | 50 mbar for 4 h, 55 mbar for 16 h, 50 mbar rest | 60 mbar | 70 mbar | 80 mbar |
| AV, 24 h | 343.89 | 339.99 | 316.34 | 311.03 |

TABLE 2-continued

Hydrolysis of C8C10 methyl-ester under different pressure conditions

| | Experiment | | | |
|---|---|---|---|---|
| | 2A | 2B | 2C | 2D |
| Hydrolysis Rate (%) | 96.9 | 95.8 | 89.1 | 87.6 |

Figure 11:
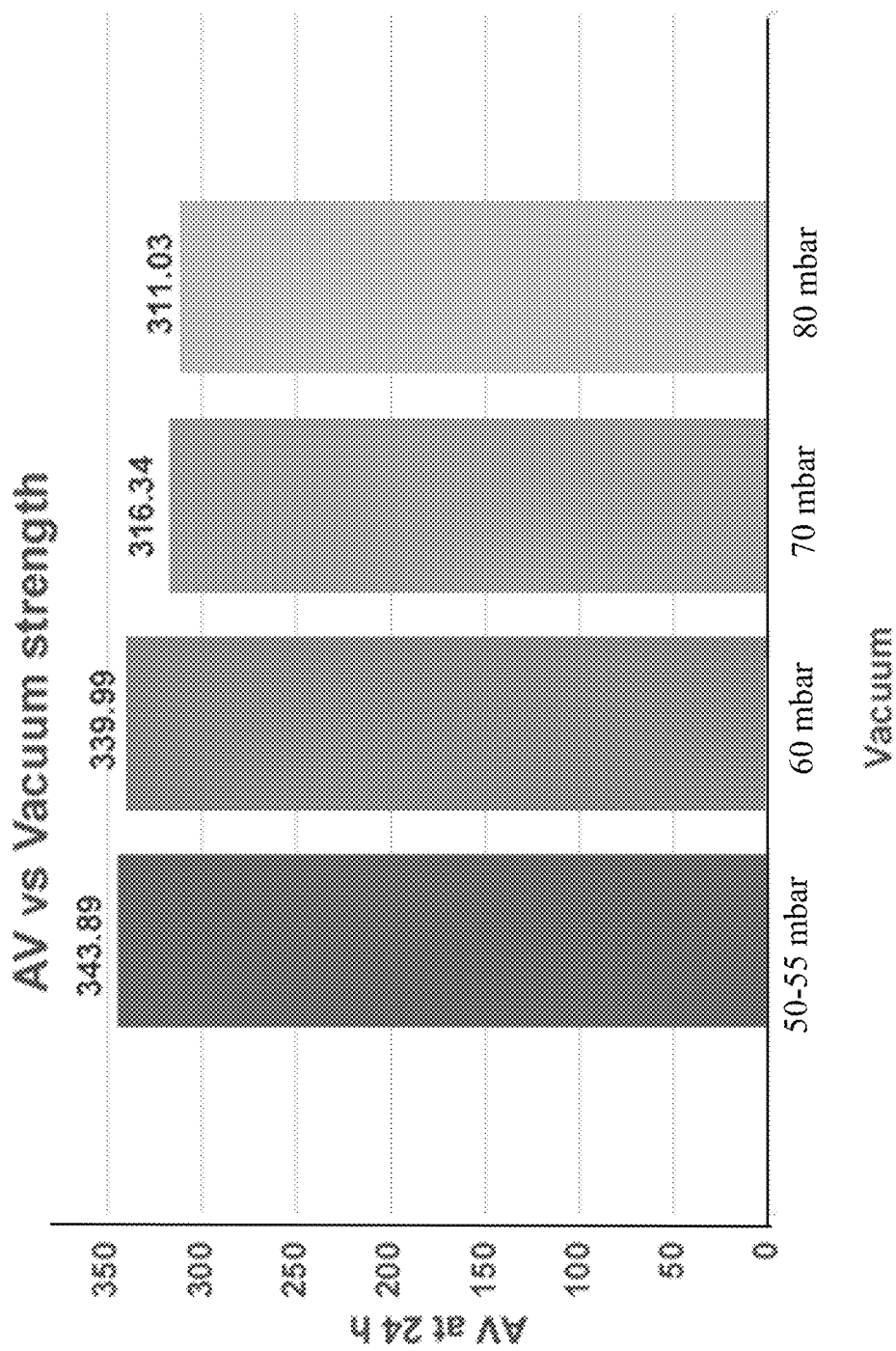
FIG. 11 shows a chart of the acid values at different vacuum strengths.

The rate of the hydrolysis of the C8/10-OMe ester was studied using the following experimental setup: 20 g of C8/10-OMe, 40 mL of water, 100 ppm of LTL3 lipase, 45° C., under different vacuum (50-55, 60, 70 or 80 mbar). The results are shown in the table above and in FIG. 11. It may be seen that with a lower operating pressure, the acid value increases, in other words there is a higher rate of hydrolysis.

Example 8: Biodiesel Production by LTL3 (SEQ ID No. 3) from Palm Fatty Acid Distillate 0.75 gram of PFAD (palm fatty acid distillate) and 0.25 g of PME (palm methyl ester) were added to a reactor, followed by water, methanol (MeOH) and the LTL3 enzyme. The mixture was incubated at 37° C. with stirring at 350 rpm for 24 hours. The heavy phase (containing glycerol, water and enzyme) was removed by centrifugation at 4,000 g for 10 mins, and the acid value of the light phase (containing PME and unreacted PFAD) was tested by titration with 0.1 M NaOH. PFAD is a residue after distillation of palm oil, and is a by product of the palm oil refining process, by finding means to further process PFAD, the efficiency of the entire palm oil refining process increases. NaOH is provided in ppm as the weight of NaOH with respect to the weight of the PFAD and PME.

For the enzyme, the percentage value is the volume of liquid enzyme solution to the weight of the oil. The enzyme dosage in ppm is the mass of the enzyme protein relative to the mass of the oil (or substrated).

Enzyme dosage $(ppm) =$ $$\frac{\text{Volume of enzyme solution} \times \text{enzyme concentration}}{\text{weight of } PFAD + PME}$$

TABLE 3

Conversion of PFAD into biodiesel by LTL3 with different amounts of H₂O

| Experiment | 3A | 3B | 3C | 3D | 3E | 3F | 3G | 3H | 3I |
|---|---|---|---|---|---|---|---|---|---|
| PFAD + PME (75:25) (g) | 1 | 1 | 1 | 1 | 1 | 1 | 1 | 1 | 1 |
| MeOH | | | | 170 μL in ten times | | | | | |
| Total water (weight %) | 0.57% | 1% | 2% | 3% | 4% | 6% | 8% | 10% | 12% |
| NaOH | | | | | 40 ppm | | | | |
| LTL3 | | | | | 0.5% (110 ppm) | | | | |
| Enzyme AV 24 h | 89.7 | 16.2 | 13.89 | 9.91 | 8.07 | 7.97 | 8.83 | 9.67 | 10.18 |

Experiment conditions: Reaction temperature 37° C., 2000 rpm thermomixer, overnight The water content in the range of 3-12 weight % allows the esterification to occur to provide the product ester at good rates, The water content range of 4-8 weight %, in particular 4-6 weight % gave better results. A water dosage of 6% provided the lowest acid value, i.e. the most ester product formed.

The water dosage affects the esterification reaction. Without being bound by theory, it is believed water provides a medium to dissolve NaOH and the oil-water interface required by most lipases to be active and function better. Also, PFAD contains small amount of MAG, DAG and TAG. Although lipases may catalyse transesterification, the reaction route of first hydrolysis of DAG/DAG/TAG to free fatty acids and then esterification of these fatty acids to produce ester may be more efficient for certain lipases leading to uncertainty as to whether a lipase may actually work or have sufficient enzymatic activity. In addition, if the water content is too high, the reverse hydrolysis reaction may become more favourable and decreases the rate of esterification.

Bases other than sodium hydroxide may possibly be used as well including other inorganic bases like metal hydroxides and ammonium hydroxide, organic bases, and polymer supported bases. Examples of metal hydroxides include the Group 1 metal (alkali metal) hydroxide, Group 2 (alkali earth) metal hydroxide and Group 3 metal hydroxide. Examples of possible organic bases include alkyl and aryl amines, quarternary ammonium hydroxide. Bases like sodium hydroxide and potassium hydroxide are more commonly used but need not be limited as such.

TABLE 4

Conversion of PFAD into biodiesel by LTL3 with different amounts of NaOH

| | Experiment | | | | |
|---|---|---|---|---|---|
| | 4A | 4B | 4C | 4D | 4E |
| PFAD + PME (75:25) (g) | 1 | 1 | 1 | 1 | 1 |
| MeOH | 170 μL in ten times with 30 min interval, totally 1.7 mL | | | | |
| Total water (weight %) | 6% | 6% | 6% | 6% | 6% |
| NaOH | 0 | 40 ppm | 80 ppm | 200 ppm | 400 ppm |
| LTL3 | 0.5% | 0.5% | 0.5% | 0.5% | 0.5% |

TABLE 4-continued

Conversion of PFAD into biodiesel by LTL3 with different amounts of NaOH

| | Experiment | | | | |
|---|---|---|---|---|---|
| | 4A | 4B | 4C | 4D | 4E |
| Enzyme AV 24 h | (110 ppm) 10.81 | (110 ppm) 9.43 | (110 ppm) 9.12 | (110 ppm) 9.09 | (110 ppm) 8.81 |

Experiment conditions: Reaction temperature 37° C., 2000 rpm with thermomixer, overnight From the results, it may be seen that as the amount of base present rises from 0 to 400 ppm, the acid value decreases, i.e. more acid is converted to the ester. 200 ppm NaOH was preferred as more NaOH led to more soap being formed which causes emulsions in the mixture.

Figure 8:
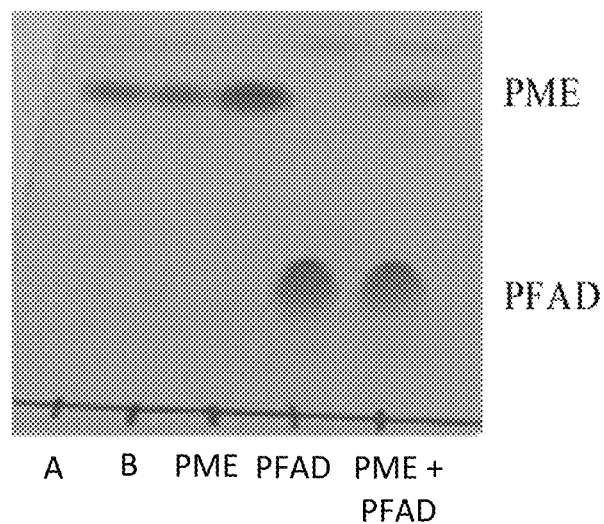
FIG. 8 shows a TLC analysis of LTL3-mediated biodiesel conversion.

An AV value of 6.0 corresponds to about 97% conversion of PFAD into PME, which is comparable to Eversa® transform 2.0 performance. FIG. 8 shows a thin layer chromatography (TLC) sample of the reaction comparing the starting material and products. It may be seen that the conversion to PME is almost complete.

TABLE 5

Conversion of PFAD into biodiesel with different amounts of LTL3

| | Experiment | | | |
|---|---|---|---|---|
| | 5A | 5B | 5C | 5D |
| PFAD + PME (7.5:2.5) (g) | 1 | 1 | 1 | 1 |
| MeOH | 170 μL in ten times | | | |

TABLE 5-continued

Conversion of PFAD into biodiesel with different amounts of LTL3

| | Experiment | | | |
|---|---|---|---|---|
| | 5A | 5B | 5C | 5D |
| Total water (weight %) | 6% | 6% | 6% | 6% |
| NaOH | 40 ppm | 40 ppm | 40 ppm | 40 ppm |
| LTL3 Enzyme | 0.1% (22 ppm) | 0.2% (44 ppm) | 0.5% (110 ppm) | 1% (220 ppm) |
| AV 24 h | 12.03 | 9.53 | 7.04 | 7.60 |

Experiment conditions: Reaction temperature 37° C. overnight

It may be seen that even at a low dosage of 22 ppm, the esterification proceeded satisfactorily after 24 hours. The enzyme dosage of 110 ppm and 220 ppm provided the ester product in better yields. As the LTL3 enzyme catalyses both the esterification and hydrolysis reaction, it may be possible that the effect on the ester hydrolysis may be larger than ester synthesis, leading to a shift in the equilibrium depending on the enzyme dosage, which result in a slightly higher AV.

TABLE 6

LTL3 mediated conversion of PFAD into PME

| Experiment | 6A | 6B | 6C | 6D | 6E | 6F |
|---|---|---|---|---|---|---|
| PFAD (mg) | 750 | 750 | 750 | 750 | 750 | 750 |
| MeOH | | | 170 μL in 10 times | | | |
| Total water (weight %) | 8 | 8 | 8 | 8 | 8 | 8 |
| LTL3 Enzyme (weight %) | 0.1% (22 ppm) | 0.2% (44 ppm) | 0.5% (110 ppm) | 1% (220 ppm) | 2% (440 ppm) | 3% (660 ppm) |
| AV 21 h | 20.77 | 14.93 | 12.53 | 12.04 | 10.34 | 9.75 |

Reaction temperature 45° C. 30 mins, 40° C. overnight. The LTL3 enzyme concentration was about 22 mg/mL The best result was obtained when 3% of the LTL3 enzyme was used to provide an acid value of 9.75. Smaller quantities of triacylglycerol (TAG), monoacylglycerol (MAG) and diacylglycerol (DAG) were also observed on TLC. PFAD contains small amount of MAG, DAG and TAG. Although lipases may catalyse transesterification, the reaction route of first hydrolysis of DAG/DAG/TAG to free fatty acids and then esterification of these fatty acids to produce ester may be more efficient for certain lipases leading to uncertainty as to whether a lipase may actually work or have sufficient enzymatic activity.

Example 9: Biodiesel Production by LTL3 from Acid Oil

Acid oil is generated from an alkaline wash of vegetable oil, such as soybean oil, to remove fatty acids and generates soap stock. The soap stock is reacidified to form a product called acid oil. Acid oil is produced as a by-product in vegetable oil refining thus the present process provides a means to use the acid oil and improves the efficiency of the vegetable oil refining process. NaOH is provided in ppm as the weight of NaOH with respect to the weight of the acid oil used.

TABLE 7

Conversion of acid oil into FAME by LTL3 under different amount of NaOH

| Experiment | 7A | 7B | 7C | 7D | 7E | 7F | 7G |
|---|---|---|---|---|---|---|---|
| Acid oil (mg) | 750 | 750 | 750 | 750 | 750 | 750 | 750 |
| MeOH | | | | 170 μL in ten times | | | |
| Total water (weight %) | | | | 8% | | | |
| NaOH (ppm) | 0 | 53 | 107 | 160 | 267 | 427 | 533 |

TABLE 7-continued

Conversion of acid oil into FAME by LTL3 under different amount of NaOH

| Experiment | 7A | 7B | 7C | 7D | 7E | 7F | 7G |
|---|---|---|---|---|---|---|---|
| LTL3 Enzyme | | | | 50 ppm | | | |
| AV 21 h | 122.16 | 120.46 | 70.44 | 18.84 | 9.84 | 15.72 | 15.28 |

Experiment conditions: Reaction temperature 37° C. overnight

It may be observed that the conversion of acid oil improves greatly with the addition of NaOH. However, an excessive amount of NaOH may cause direct hydrolysis of the ester. Better acid oil conversion rates were observed for the experiments with 160 to 533 ppm NaOH.

TABLE 8

Conversion of acid oil into FAME by LTL3 with different amounts of water.

| Experiment | 8A | 8B | 8C | 8D | 8E | 8F | 8G |
|---|---|---|---|---|---|---|---|
| Acid oil (mg) | 750 | 750 | 750 | 750 | 750 | 750 | 750 |
| MeOH | | | | 170 μL in ten times | | | |
| Total water (weight %) | 1.2% | 2% | 4% | 6% | 8% | 10% | 12% |
| NaOH (ppm) | 267 | 267 | 267 | 267 | 267 | 267 | 267 |
| LTL3 Enzyme | 50 ppm | 50 ppm | 50 ppm | 50 ppm | 50 ppm | 50 ppm | 50 ppm |
| AV 24 h | 17.98 | 26.56 | 18.38 | 17.19 | 9.48 | 9.46 | 10.02 |

Experiment conditions: Reaction temperature 37° C., 2000 rpm with Eppendorf® thermomixer, 24 h.

It may be observed that the conversion of acid oil to ester is more efficient in the presence of 6% to 12% of water. In particular, a water content of 8-10% provides the best activity with LTL3.

TABLE 9

Conversion of acid oil into FAME with different amounts of LTL3

| Experiment | 9A | 9B | 9C | 9D | 9E |
|---|---|---|---|---|---|
| Acid oil (g) | 0.75 | 0.75 | 0.75 | 0.75 | 0.75 |
| Total water dosage (weight %) | 8% | 8% | 8% | 8% | 8% |
| NaOH (ppm) | 53 | 53 | 53 | 53 | 53 |
| LTL3 dosage (ppm) | 10 | 20 | 50 | 100 | 150 |
| MeOH (uL) | 170 × 10 times | 170 × 10 times | 170 × 10 times | 170 × 10 times | 170 × 10 times |
| AV, 22 h | 26.02 | 16.59 | 9.58 | 9.06 | 8.91 |

Experiment conditions: Reaction temperature 37° C., 2000 rpm with Eppendorf® thermomixer, 24 h.

A LTL3 dosage as low as 50 ppm provided a product with an acid value below 10 after 22 hours. Alternatively, a longer reaction time may possibly achieve the same acid value.

The invention claimed is:

1. A method of producing a medium chain fatty acid by hydrolysis, the method comprising:
(a) providing a polypeptide with at least 90% degree of identity to SEQ ID NO: 3; and
(b) contacting the polypeptide with a medium chain fatty acid ester and water such that the polypeptide enzymatically hydrolyzes the medium chain fatty acid ester to produce the medium chain fatty acid, wherein the medium chain fatty acid ester is a monoester, wherein and the medium chain fatty acid has an acid value of at least 320.

2. The method according to claim 1, wherein the medium chain fatty acid ester is at least one selected from a caprylate ester, a caprate ester, and a laurate ester.

3. The method according to claim 2, wherein the medium chain fatty acid ester is a combination of a caprylate ester and a caprate ester.

4. The method according to claim 1, wherein the contacting step is performed under at least one of the following conditions:
   (a) a temperature of 20° C. to 70° C.;
   (b) a pH of 3 to 9;
   (c) reacting the medium chain fatty acid ester with the polypeptide is performed at a pressure of 100 mbar and lower.

5. The method according to claim 1, wherein the polypeptide is present in a concentration of 30 ppm or greater.

6. The method according to claim 1, wherein the polypeptide has at least 95% degree of identity to the SEQ ID NO: 3.

7. The method according to claim 1, wherein the monoester is a methyl ester or an ethyl ester.

* * * * *

SEQUENCE LISTING

```
<160> NUMBER OF SEQ ID NOS: 4

<210> SEQ ID NO 1
<211> LENGTH: 291
<212> TYPE: PRT
<213> ORGANISM: Thielavia terrestris

<400> SEQUENCE: 1

Ala Pro Thr Ser Arg Arg Gln Asp Ala Val Thr Thr Gln Gln Leu Asp
1               5                   10                  15

Asn Leu Lys Leu Phe Val Gln Trp Ser Val Ala Ala Thr Cys Asn Ser
            20                  25                  30

Glu Lys Ser Ala Gly Gln Pro Val Thr Cys Pro Pro Gly Gln Cys Ser
        35                  40                  45
```

```
Leu Phe Glu Ser His Asn Ala Thr Val Val Ala Ser Phe Ile Gly Thr
 50                  55                  60

Leu Leu Asp Thr Arg Gly Phe Val Gly Val Asp Pro Val Ser Gln Gln
 65                  70                  75                  80

Ile Val Val Ser Phe Arg Gly Thr Thr Ser Val Gln Asn Trp Ile Ala
                 85                  90                  95

Asp Leu Thr Phe Val Gln Val Pro Cys Asp Leu Thr Pro Gly Cys Leu
            100                 105                 110

Val His Thr Gly Phe Trp Gly Ser Trp Gly Glu Val Ala Ala Arg Thr
            115                 120                 125

Leu Ala Ala Val Arg Asp Ala Lys Ala Ala His Pro Ala Tyr Ser Val
130                 135                 140

Ile Val Thr Gly His Ser Leu Gly Gly Ala Val Ala Thr Leu Ala Ala
145                 150                 155                 160

Ala Tyr Leu Arg Arg Ala Gly Phe Ala Ala Asp Leu Tyr Thr Tyr Gly
                165                 170                 175

Ser Pro Arg Ile Gly Asn Ala Ala Phe Val Glu Phe Val Thr Ala Gln
            180                 185                 190

Pro Gly Gly Glu Tyr Arg Val Thr His Thr Asp Asp Pro Val Pro Arg
            195                 200                 205

Leu Pro Pro Leu Val Ala Asn Tyr Arg His Thr Ser Pro Glu Tyr Trp
210                 215                 220

Ile Ser Ser Thr Ser Gln Gly Pro Val Thr Pro Ala Asp Val Gln Tyr
225                 230                 235                 240

Cys Pro Gly Tyr Ala Asn Val Gln Cys Asn Gly Gly Thr Glu Gly Leu
                245                 250                 255

Asp Ile Asp Ala His Asn Trp Tyr Phe Gln Pro Leu Asp Gly Cys Ser
            260                 265                 270

Ala Arg Gly His Ala Ala Gln Glu Gly Gly Arg Gly Ile Ile Thr Ser
            275                 280                 285

Ala Gly Ser
   290

<210> SEQ ID NO 2
<211> LENGTH: 873
<212> TYPE: DNA
<213> ORGANISM: Thielavia terrestris

<400> SEQUENCE: 2
gctccaactt ctagaagaca agatgctgtt actactcaac aattggataa cttgaagttg      60
tttgttcaat ggtctgttgc tgccacttgt aactccgaga agtccgctgg acagcctgtt     120
acctgtcctc caggacagtg ttccctgttc gagtcccaca acgctactgt tgttgcttct     180
ttcatcggta ccttgttgga cactagagga ttcgtcggtg tcgaccctgt ctcacagcag     240
atcgttgttt ctttcagagg tactacctct gttcagaact ggattgctga tttgaccttc     300
gttcaagttc cttgtgactt gaccectggt tgtttggttc atactggttt ctggggttcc     360
tggggtgaag tcgccgctcg taccttggcc gctgttagag acgccaaggc cgctcaccca     420
gcttactcag tcatcgtcac cggtcatagt ttggtggtg ctgttgctac cttgccgcc      480 gcttacctga aagagctggt ttcgctgct gatttgtaca cttacggttc tccaagaatt     540
ggtaacgctg ccttcgtcga gtttgttact gcccagccag gtggtgagta cagagttacc     600
cacaccgacg acccagttcc aagactgcca cctttggtcg ctaactacag acacacttcc     660
ccagaatact ggatttcctc tacttcccag ggtccagtta ccccagctga tgttcaatac     720
```

```
tgtccaggtt acgctaacgt tcaatgtaac ggtggtaccg agggtttgga cattgatgct    780
cataactggt actttcaacc attggatggt tgctctgcta gaggtcatgc tgctcaagaa    840
ggtggtagag gtattattac ttctgctggt tct                                 873
```

<210> SEQ ID NO 3
<211> LENGTH: 431
<212> TYPE: PRT
<213> ORGANISM: Lasiodiplodia theobromae

<400> SEQUENCE: 3

```
Ala Pro Ala Pro Val Pro Glu Asn Gly Leu Glu Lys Arg Gln Ser Leu
1               5                   10                  15

Ser Ser Val Leu Ser Ala Leu Ser Gly Leu Thr Glu Pro Thr Ala Ile
            20                  25                  30

Leu Ser Gln Leu Glu Ala Val Glu Ala Thr Ser Thr Pro Thr Ser Val
        35                  40                  45

Glu Gln Ala Gln Glu Gln Leu Glu Ala Ile Tyr Gly Thr Thr Pro Thr
    50                  55                  60

Asn Ile Phe Glu Asn Ile Ala Gln Gln Ile Ala Asp Gly Leu Ser Thr
65                  70                  75                  80

Leu Thr Ile Val Gln Ala Leu Gly Phe Ser Pro Ser Gly Glu Asn Ser
                85                  90                  95

Glu Thr Asn Ser Asn Thr Arg Glu Pro Ser Thr Thr Ile Tyr Pro Lys
            100                 105                 110

Lys Ser Ser Ser Asp Ala Pro Tyr Ser Ile Thr Glu Glu Leu Arg
        115                 120                 125

Gln Ala Ile Tyr Ile Pro Ser Asp Phe Thr Tyr Gly Asp Lys Pro Pro
    130                 135                 140

Val Ile Phe Val Pro Gly Thr Gly Ser Tyr Gly Gly Ile Ser Phe Gly
145                 150                 155                 160

Ser Asn Leu Arg Lys Leu Leu Thr Gly Val Ser Tyr Ala Asp Pro Val
                165                 170                 175

Trp Leu Asn Val Pro Asp Ala Leu Leu Arg Asp Ala Gln Thr Asn Gly
            180                 185                 190

Glu Phe Val Ala Tyr Ala Ile Asn Tyr Ile Ser Gly Ile Ser Gly Asp
        195                 200                 205

Ala Asn Val Ser Val Val Ser Trp Ser Gln Gly Gly Leu Asp Thr Gln
    210                 215                 220

Trp Ala Phe Thr Tyr Trp Pro Ser Thr Arg Ala Leu Val Ser Asp Phe
225                 230                 235                 240

Val Pro Val Ser Pro Asp Phe His Gly Thr Val Leu Ala Asn Val Ile
                245                 250                 255

Cys Leu Asn Pro Gly Ala Gly Gly Val Gly Leu Gly Pro Cys Ala Pro
            260                 265                 270

Ala Val Leu Gln Gln Glu Tyr Asn Ser Asn Phe Val Thr Ala Leu Arg
        275                 280                 285

Ala Ala Gly Gly Ala Asp Ala Tyr Val Pro Thr Thr Ser Val Phe Ser
    290                 295                 300

Gly Phe Leu Asp Glu Ile Val Gln Pro Gln Ser Gly Thr Gly Ala Ser
305                 310                 315                 320

Ala Tyr Ile Asn Asp Ala Arg Gly Val Gly Thr Thr Asn Ala Glu Val
                325                 330                 335

Gln Val Val Cys Lys Gly Lys Gly Pro Ala Gly Gly Phe Tyr Thr His
```

```
                       340                 345                 350
Glu Ser Leu Leu Val Asn Pro Leu Thr Tyr Ala Leu Leu Val Asp Ala
            355                 360                 365

Leu Thr His Asp Gly Pro Gly Ser Val Asp Arg Leu Asp Leu Asp Thr
        370                 375                 380

Val Cys Ser Thr Val Val Ala Pro Gly Leu Gly Leu Asp Ala Leu Leu
385                 390                 395                 400

Glu Ile Glu Gly Val Asn Val Leu Ala Ala Val Asn Leu Leu Thr Tyr
                405                 410                 415

Ser Asp Arg Arg Leu Ala Glu Pro Ala Leu Met Ser Tyr Ala Ala
                420                 425                 430

<210> SEQ ID NO 4
<211> LENGTH: 1296
<212> TYPE: DNA
<213> ORGANISM: Lasiodiplodia theobromae

<400> SEQUENCE: 4
gccccagccc ctgtccctga aaatgggctc gagaagaggc agtccctgag cagcgtcctg      60
agcgccctca gtggcctgac cgaacctacg gccatcttgt ctcagctcga ggcggttgaa     120
gcgacatcga cgcccaccag cgtcgagcag gcgcaggagc agctcgaggc catctacggg     180
acgacaccaa ccaacatctt cgagaacatc gcgcagcaaa tcgccgacgg actgtcgacg     240
ctgaccatcg tccaagccct cggcttctcc cccagcggcg agaactcgga gaccaacagc     300
aacacgcgcg aaccgtcgac gaccatctac cccaagaagt cgtcctccga cgcccccctat    360 tccatcactg aggaagagct ccgccaagcc atctacatcc cctccgactt cacgtacggc     420
gacaagccgc cggtcatctt cgtgccgggc acgggctcgt acggcggcat cagcttcgga     480
tcgaacctgc gcaagctgct gacgggcgtg tcgtacgcgg acccggtatg gctcaacgtg     540
ccggacgcgc tgctgcgcga cgcgcagacg aacggcgagt cgtggcgta cgccatcaac      600 tacatctcgg gcatatccgg cgacgccaac gtgtcggtcg tctcgtggtc gcagggcggg     660
ctggacacgc agtgggcttt tacttattgg ccgtcgacgc gcgccctggt ctccgacttc     720
gtgcccgtca gccggactt ccacggcacc gtcctggcta atgtcatctg cctcaacccg      780
ggcgccggtg gtgttggtct gggcccctgc gcgcccgcgg tgctgcagca ggaatacaac     840
agcaacttcg tcacggccct gcgcgcggct ggtggtgcgg acgcctatgt gccgacgacg     900
tctgttttct ccggcttcct cgacgagatc gtccagccgc agtccggcac cggcgcgtcc     960
gcgtacatca atgatgctag gggtgtgggc acgaccaatg ctgaggtgca ggtcgtgtgc    1020
aagggcaagg gtcccgctgg cggtttttac acccacgaga gcttgctggt caacccgctg    1080
acctatgctc tcctcgtcga tgccttgacc cacgatgggc ccggcagtgt ggacaggctg    1140
gatctggata ccgtgtgctc gaccgtcgtg gcgcccggcc tgggactgga tgcgttgttg    1200
gagattgagg gcgtgaatgt tctggcggct gtcaatctgt tgacctactc agataggagg    1260
ttggctgagc cggcgctgat gtcatatgcg gcttaa                              1296
```